United States Patent
Krueger et al.

(10) Patent No.: US 12,385,888 B2
(45) Date of Patent: Aug. 12, 2025

(54) INERT FLUID ASSAYS FOR SEALED CORE RECOVERY

(71) Applicant: CONOCOPHILLIPS COMPANY, Houston, TX (US)

(72) Inventors: Martin C. Krueger, Houston, TX (US); Shaina A. Kelly, Houston, TX (US); Gerald E. Michael, Houston, TX (US); Thiago B. Simoes Correa, Houston, TX (US); Russell Bone, Houston, TX (US)

(73) Assignee: ConocoPhillips Company, Houston, TX (US)

( * ) Notice: Subject to any disclaimer, the term of this patent is extended or adjusted under 35 U.S.C. 154(b) by 237 days.

(21) Appl. No.: 17/888,089

(22) Filed: Aug. 15, 2022

(65) Prior Publication Data

US 2023/0086532 A1  Mar. 23, 2023

Related U.S. Application Data

(60) Provisional application No. 63/244,953, filed on Sep. 16, 2021.

(51) Int. Cl.
*G01N 30/68* (2006.01)
*G01N 9/00* (2006.01)
(Continued)

(52) U.S. Cl.
CPC .............. *G01N 30/68* (2013.01); *G01N 9/00* (2013.01); *G01N 33/2823* (2013.01); *G01N 2030/025* (2013.01)

(58) Field of Classification Search
None
See application file for complete search history.

(56) References Cited

U.S. PATENT DOCUMENTS

| | | | |
|---|---|---|---|
| 3,986,555 | A | 10/1976 | Roberstson |
| 4,230,192 | A | 10/1980 | Pfannkuche |

(Continued)

FOREIGN PATENT DOCUMENTS

| | | | |
|---|---|---|---|
| GB | 2184835 A | 7/1987 | |
| GB | 2293653 A | 4/1996 | |

(Continued)

OTHER PUBLICATIONS

International Search Report and Written Opinion for application No. PCT/US22/40338 dates Dec. 19, 2022.

(Continued)

*Primary Examiner* — Laura Martin
*Assistant Examiner* — Mark A Shabman
(74) *Attorney, Agent, or Firm* — Boulware & Valoir PLLC

(57) ABSTRACT

Methods of determining if a test fluid is inert to reservoir oil at RTP, by assaying a composition, density and bubble or dew point of live oil to generate a first dataset, equilibrating a sample of live oil with a test fluid at RTP to generate an oil phase; assaying a composition, density and bubble or dew point of the oil phase to generate a second dataset; comparing the first and second datasets, wherein significant changes in the datasets indicate that the test fluid is not inert to reservoir oil at RTP. By contrast, if there are no significant changes, the test fluid is inert, and would therefore be suitable to collecting core samples at RTP. Various options for inert fluids are also provided.

17 Claims, 13 Drawing Sheets

(51) Int. Cl.
*G01N 30/02* (2006.01)
*G01N 33/28* (2006.01)

(56) References Cited

U.S. PATENT DOCUMENTS

| | | | |
|---|---|---|---|
| 4,256,192 A | 3/1981 | Aumann | |
| 4,258,803 A | 3/1981 | Thompson et al. | |
| 4,573,342 A | 3/1986 | Jones | |
| 4,649,737 A | 3/1987 | Jones | |
| 4,702,168 A | 10/1987 | Colle et al. | |
| 4,950,844 A | 8/1990 | Hallmark | |
| 5,193,059 A | 3/1993 | Tiab et al. | |
| 5,263,360 A | 11/1993 | Blauch et al. | |
| 5,265,462 A | 11/1993 | Blauch et al. | |
| 5,297,420 A | 3/1994 | Gilliland et al. | |
| 5,359,194 A | 10/1994 | Moss | |
| 5,741,959 A | 4/1998 | Garcia et al. | |
| 6,642,056 B1* | 11/2003 | Correra | G01N 33/2823 436/139 |
| 7,347,284 B2 | 3/2008 | Arian et al. | |
| 7,600,580 B2 | 12/2009 | Caravatte et al. | |
| 8,122,976 B2 | 2/2012 | Bartelle et al. | |
| 8,256,282 B2 | 9/2012 | Schlachter | |
| 8,230,946 B2 | 11/2012 | Crawford et al. | |
| 8,307,704 B2 | 11/2012 | Georgi et al. | |
| 8,356,510 B2 | 1/2013 | Coenen | |
| 8,453,766 B2 | 6/2013 | Graterol et al. | |
| 8,621,920 B2 | 1/2014 | Reid et al. | |
| 9,051,804 B2 | 6/2015 | Reid et al. | |
| 9,243,466 B2 | 1/2016 | Klomp | |
| 9,291,541 B2 | 3/2016 | Kim et al. | |
| 9,376,879 B2 | 6/2016 | Mizuguchi | |
| 9,506,307 B2 | 11/2016 | Kinsella | |
| 9,745,811 B2 | 8/2017 | Wesemeier et al. | |
| 9,828,820 B2 | 11/2017 | Gupta et al. | |
| 9,874,063 B2 | 1/2018 | Arian et al. | |
| 9,926,756 B2 | 3/2018 | Wesemeier et al. | |
| 9,951,574 B2 | 4/2018 | Westacott et al. | |
| 10,047,580 B2 | 8/2018 | Morgan et al. | |
| 10,174,613 B2 | 1/2019 | Quintero et al. | |
| 10,221,684 B2 | 3/2019 | Westacott et al. | |
| 10,260,300 B2 | 4/2019 | Dorovsky et al. | |
| 10,301,936 B2 | 5/2019 | Westacott et al. | |
| 10,317,351 B2 | 6/2019 | Chong et al. | |
| 10,550,655 B2 | 2/2020 | Jones et al. | |
| 10,761,157 B2 | 9/2020 | Chen et al. | |
| 2010/0126266 A1 | 5/2010 | Coenen | |
| 2013/0197809 A1* | 8/2013 | Jones | G01N 1/00 73/864.91 |
| 2014/0090835 A1 | 4/2014 | Griffin | |
| 2014/0130581 A1* | 5/2014 | Ovalles | C09K 8/04 208/309 |
| 2014/0208826 A1* | 7/2014 | Larter | G01N 11/00 356/70 |
| 2015/0354352 A1 | 12/2015 | Ezzat et al. | |
| 2017/0089158 A1* | 3/2017 | Gupta | G01N 33/24 |
| 2018/0148988 A1 | 5/2018 | Dusterhoft et al. | |
| 2018/0298709 A1* | 10/2018 | Gupta | G01V 5/04 |
| 2018/0371904 A1 | 12/2018 | Zuilekom et al. | |

FOREIGN PATENT DOCUMENTS

| | | |
|---|---|---|
| WO | 2019070252 A1 | 4/2019 |
| WO | 2019090316 A1 | 5/2019 |

OTHER PUBLICATIONS

Kenyon, W.E. Petrophysical Principles of Applications of NMR Logging. The Log Analyst (2009) 38 (2): 21-43.
Murphy, D.P. 1995. NMR logging and core analysis—simplified. World Oil (1995) 216 (4): 65-70. OSTI ID 39931.
Woessner, D.E. The early days of NMR in the Southwest. Concepts in Magnetic Resonance (2001)13 (2): 77-102.
Zhao, T.; Verma S.; Devegowda, D.; Jayaram, V. TOC Estimation in the Barnett Shale From Triple Combo Logs Using Support Vector Machine. SEG Annual Meeting, 2015, Paper # SEG-2015-5922788.
Truax J.; Galford, J.; Moake, G.; Torres, D.; Cherry, R.; Mandal, B.; Mishra, A.; Martin, S. L.; Quintero, A. Performance of a new 2.35-in. wireline or memory quad combo for through-bit or small-hole logging. SPE Annual Technical Conference and Exhibition. 2011, Paper # SPE-147400-MS.
Clark, A. J. (2009). Determination of recovery factor in the Bakken formation, Mountrail County, ND. SPE Annual Technical Conference and Exhibition. 2009, Paper # SPE-133719-STU.
Alhashim, H. W.; Zhang, F.; Schechter, D. S.; Chen J-H. Investigation of the effect of pore size distribution on the produced oil from surfactant-assisted spontaneous imbibition in ULRs. SPE Annual Technical Conference and Exhibition. SPE-195931-MS.
Dunn, K.-J.; Bergman, D.J.; Latorraca, G.A. Nuclear Magnetic Resonance Petrophysical and Logging Applications. (2002) vol. 32, New York: Handbook of Geophysical Exploration: Seismic Exploration, Pergamon Press.

* cited by examiner

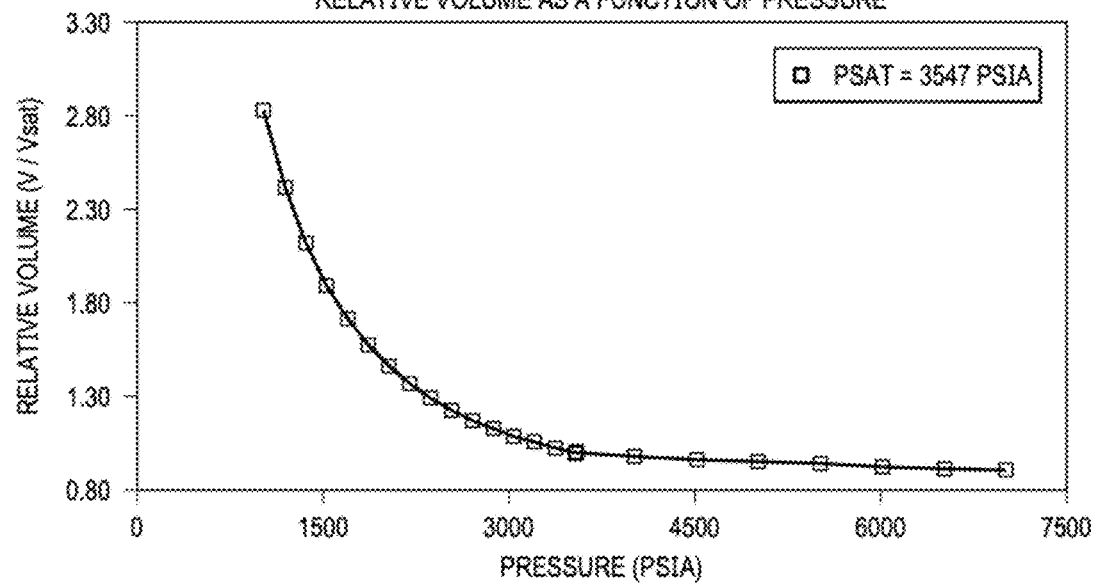
FIG. 1.1
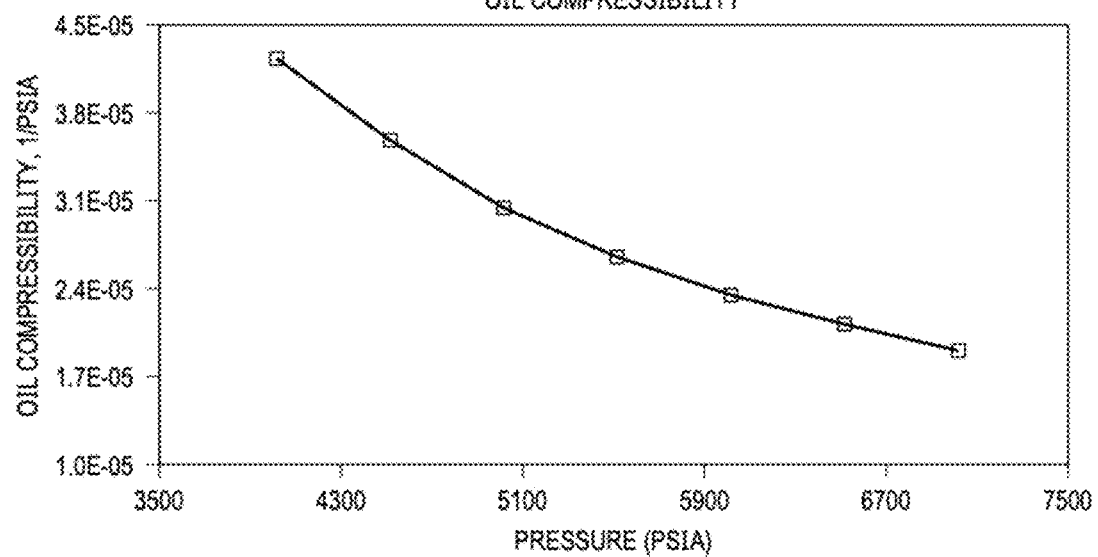
FIG. 1.2

FIG. 2.1
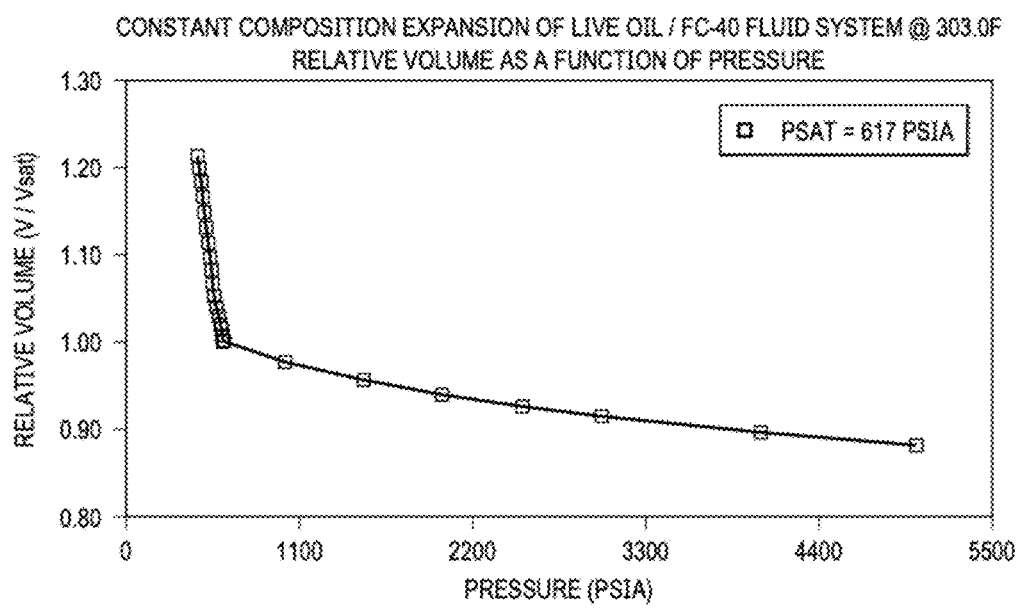
FIG. 2.2
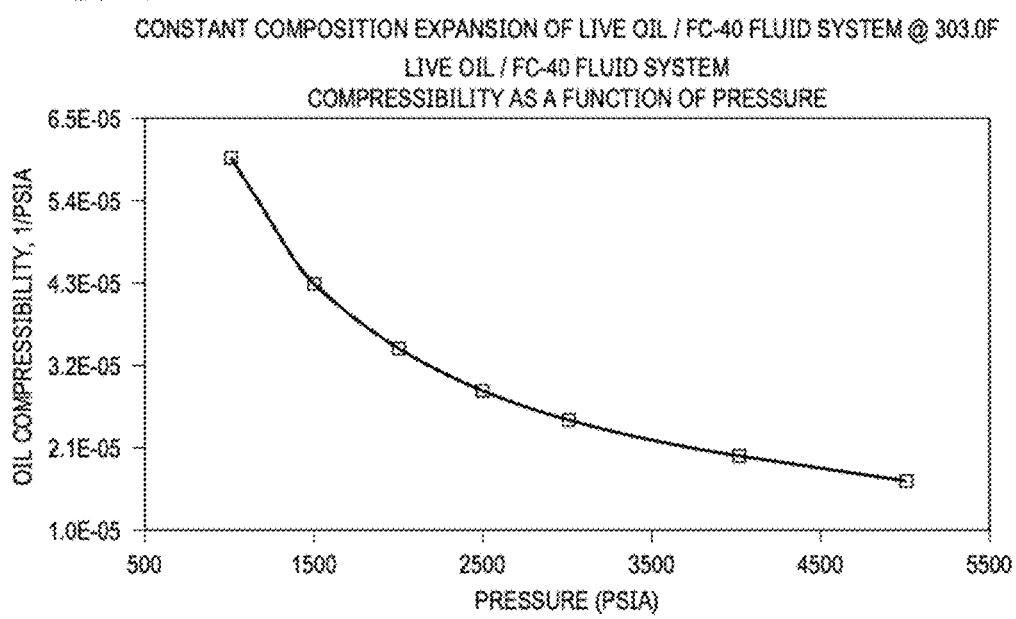

CONSTANT COMPOSITION EXPANSION PICTURES
OIL / FC-40 INTERFACE FLUID CHANGE DURING MECHANICAL MIXING

PRESSURE 5000.2 Psi
VOLUME 373.823 cc
TEMPERATURE 304.1 °F

OIL

CONSTANT COMPOSITION EXPANSION PICTURES
OIL / FC-40 INTERFACE AT SATURATION PRESSURE

PRESSURE 605.2 Psi
VOLUME 421.721 cc
TEMPERATURE 303.0 °F

OIL

INERT FLUID ASSAYS FOR SEALED CORE RECOVERY

PRIOR RELATED APPLICATIONS

This application claims priority to U.S. Ser. No. 63/244,953, filed Sep. 16, 2021, and incorporated by reference in its entirety for all purposes.

FIELD OF THE DISCLOSURE

This disclosure provides methods of testing core preservation fluids for drilling core samples and returning them to the surface in an unchanged condition.

BACKGROUND OF THE DISCLOSURE

One of the ways of studying rock characteristics is to drill and analyze a core sample from a reservoir. Similar to a drill bit, the rotary coring bit consists of solid metal with diamonds or tungsten for cutting at the reservoir rock, but unlike a drill bit, a rotary coring bit has a hollow center. The cutting apparatus thus surrounds the hollow center, called the core barrel, where the core sample is stored. The core barrel is made up of an inner and outer barrel separated by ball bearings, which allows the inner barrel to remain stationary and retain the core sample, while the outer barrel is rotated by the drill string and cuts the core. The core catcher is located within the core barrel and has finger-like apparatuses that move the core sample farther into the barrel and keep it from falling back into the well. After the core sample has been cut from the well, the drill string is raised, and the rotary coring bit, barrel and catcher are removed, and the core sample is retrieved. The drill bit is reattached, and drilling can commence again.

However, obtaining an unaltered core sample from a reservoir with these simple prior art devices remains challenging. As the core is retrieved from deep in the reservoir, the temperature and pressure decrease which allows gases to evolve out of solution and together with free gases, expand, resulting in reservoir fluids being forced out of the core. Thus, accurate sampling, especially of fluids, is difficult, if not impossible to obtain.

To address this problem, the core samples are sometimes collected and sealed in a chamber, in a method known as "pressure coring". Pressure coring at least partially solves the problem by maintaining the core specimen at bottom-hole pressure—BHP—until the core fluids can be recovered. This concept, first proposed by Sewell in the 1930's, remained a "laboratory" tool until the late 1970's, but with the advent of ever improving technology, the method is much more popular now.

However, in pressure coring the core samples are contained in an inert fluid known as FC-40 aka FLUORI-NERT™ which was developed for electronic uses, not uses in the petroleum industry. FC-40 is a colorless, thermally stable, fully fluorinated liquid that was believed to be inert, even at reservoir temperature and pressure (RTP). With the data presented herein, we now know that it in fact solubilizes some of the lighter fractions of oil, and thus skewing the results of high pressure core analysis. The discrepancy arises from the fact that standard testing techniques are wholly inappropriate for use with a so-called "inert" fluid developed for electronic uses, as opposed to downhole uses.

This disclosure for the first time provides assays and methodology to correctly assay downhole core samples, and further develop novel inert, high density fluids for use in obtaining and analyzing reservoir core samples.

SUMMARY OF THE DISCLOSURE

FC-40 contains $C_{5-18}$ perfluorocarbon chains, that are largely inert to electronics, but less so for petroleum, which contains short, medium, and long chain hydrocarbons. Table A provides the known FC-40 properties:

TABLE A

| FC-40 1. Information on basic physical and chemical properties | |
|---|---|
| General Physical Form: | Liquid |
| Specific Physical Form: | Liquid |
| Odor, Color, Grade: | Colorless, odorless liquid. |
| Odor threshold | No Data Available |
| pH | Not Applicable |
| Melting point | Not Applicable |
| Boiling Point | 158-173° C. |
| Flash Point | No flash point |
| Evaporation rate | <1 [RefStd:BUOAC = 1] |
| Flammability (solid, gas) | Not Applicable |
| Flammable Limits(LEL) | None detected |
| Flammable Limits(UEL) | None detected |
| Vapor Pressure | 3 mmHg [@ 25° C.] |
| Vapor Density | 22.5 [@ 25° C.] [Ref St: AIR = 1] |
| Density | 1.9 g/ml |
| Specific Gravity | 1.9 [RefStd:WATER = 1] |
| Solubility in Water | Nil |
| Solubility—non-water | No Data Available |
| Partition coefficient: n-octanol water | No Data Available |
| Autoignition temperature | No Data Available |
| Decomposition temperature | No Data Available |
| Viscosity | 2 centistoke [@ 25° C.] |
| Molecular weight | No Data Available |
| Volatile Organic Compounds | [Details: Exempt] |
| Percent volatile | 100% |
| VOC Less H2O & Exempt Solvents | [Details: Exempt] |

As is apparent, FC-40 is not particularly viscous, but is fairly dense at 1.9 g/ml. Insomuch as electronics are concerned, it is fairly inert, but as demonstrated herein, light hydrocarbons have significant solubility in FC-40, even at atmospheric conditions, and at reservoir temperature and pressure (RTP), the problem is greatly exacerbated.

Thus, what is needed in the art are test methods for correctly assaying inert fluids for downhole uses. Such assays would allow the art to develop new materials that do not dissolve light hydrocarbons but is otherwise as dense and inert to the full range of petroleum constituents, especially at RTP. In the absence of an absolute inert fluid, characterization of solubility in FC-40 and other fluids at atmospheric and at reservoir conditions will provide methods to characterize interactions within the reservoir and simulate processes under reservoir conditions.

---

The invention includes any one or more of the following embodiments, any one or more of which can be combined with any other one or more in any combination(s) thereof.

A method of assaying a test fluid for collecting reservoir core samples at reservoir temperature and pressure (RTP) and determining if said test fluid is inert at RTP, said method comprising:
a) assaying live oil to generate a first dataset using methods comprising two or more of:

-continued i) determining a weight contribution of components of said live oil;
ii) determining a bubble point of said live oil;
iii) determining a density of a remaining oil when said live oil is flashed to ambient conditions; or
iv) determining a weight contribution of gaseous components flashed from said live oil;
b) assaying live oil plus a test fluid mixed together and equilibrated at RTP to form a hydrocarbon phase and a test fluid phase to generate a second dataset, using methods comprising two or more of:
i) determining a bubble point of said hydrocarbon phase;
ii) determining a weight contribution of components of said hydrocarbon phase;
iii) determining a density of a remaining hydrocarbon phase when said hydrocarbon phase is flashed to standard temperature and pressure (STP) or ambient conditions; or
iv) determining a weight contribution of gaseous components flashed from said hydrocarbon phase;
c) comparing said first dataset and said second dataset, wherein changes in said datasets after equilibration with said test fluid indicates that said test fluid is not inert, but no changes in said datasets indicates said test fluid is inert and can be used to collect reservoir core samples at RTP.

Any method described herein could also use instead of i-iv) or in addition thereto, any one or more of the following: determining total acid number (TAN), metal content, viscosity, asphaltene content, C7 content; nitrogen content, water content, carbon content, total contents; wax content; carbon residue content, conductivity, pour point, density@15° C.; salt content, sediment content, specific gravity; light end hydrocarbon content; mercaptan content; hydrogen content, total sulfur, hydrogen sulfide content or vapor pressure of said hydrocarbon phase or said remaining hydrocarbon phase.

A method of assaying a test fluid for inertness in collecting reservoir core samples at RTP, said method comprising:
a) obtaining an oil sample having a first characterization of elements, C1-C40 components, dissolved gas and density;
b) mixing said oil sample plus a test fluid to form a mixture, and equilibrating said mixture at RTP to produce a hydrocarbon phase and a test fluid phase;
c) assaying said hydrocarbon phase to determine a second characterization of elements, C1-C40 components, dissolved gas and density;
d) comparing said first characterization with said second characterization to identify changes in characterization;
e) wherein changes in characterization indicates that said test fluid is not inert, but no changes in characterization indicates said test fluid is inert and can be used to collect reservoir core samples at RTP.
A method of determining if a test fluid is inert to reservoir oil at RTP, comprising:
a) assaying a composition, density and bubble or dew point of live oil to generate a first dataset;
b) equilibrating a sample of said live oil with a test fluid at RTP to generate a hydrocarbon phase;
c) assaying a composition, density and bubble or dew point of said hydrocarbon phase to generate a second dataset;
d) comparing said first and second datasets, wherein significant changes in said dataset indicates that said test fluid is not inert to reservoir oil at RTP.

Any method herein described, wherein weight contribution is determined with gas chromatography, preferably with GC/FID, but other methods could be used including HPLC, elemental analysis, and the like.

Any method herein described, wherein density of a fluid is determined using a HPHT densitometer at RTP.

Any method herein described, wherein bubble point of a fluid is determined by stepping down the pressure from RTP and observing a pressure at which bubbles appear or by ASTM D2889-95 (2019).

Any method herein described, wherein RTP is an average temperature and pressure of a play in the reservoir.

Although we focus on composition, density, and bubble or dew points herein, other characterization methods could also be used, e.g., measuring Acidity TAN—total acid number; metals; viscosity; asphaltene, C7; nitrogen basic; water content; carbon content; nitrogen, total content; wax content; carbon residue; phosphorous content; conductivity; pour point; density@15° C.; salt; distillation; sediments, gravity; silicon content; light end hydrocarbons; sulfur, mercaptans; hydrogen content; sulfur, total; hydrogen sulfide; vapor pressure and the like. These can be added to the characterization sets or in many cases substituted therefor. For example, in our experiments it would have sufficed to test for light ends only.

As used herein, "brominated" or "fluorinated" means to replace one or more hydrogens with bromine or fluorine.

As used herein, "perbrominated" or "perfluorinated" is to combine with the maximum amount of fluorine especially in place of hydrogen.

As used herein, "high pressure" means higher than 1 atm, and includes all typical downhole pressures (e.g. up to and even beyond 25,000 psi).

As used herein, a "high temperature" means reservoir temperatures which are greater than 100° F., typically about 200-400° F. in a reservoir.

As used herein "live oil" is oil containing dissolved gas in solution that may be released from the oil solution at surface conditions. Live oil must be handled and pumped under closely controlled conditions to minimize the risk of explosion or fire.

As used herein "dead oil" is oil that has been flashed to STP or ambient conditions at the surface and no longer containing very much dissolved gas.

As used herein, "bubble point" or "bubble-point pressure" is defined as the temperature and pressure at which gas begins to break out of an under saturated oil and form a free gas phase in the matrix or a gas cap. In layman's terms it may be thought of as the pressure at which the first bubble of gas appears at a specific temperature. The phase diagram of typical black oils shows that the bubble-point pressure could be different at different temperatures and pressures dependent upon many factors including gas concentration and oil composition. Often the oil is saturated with gas when discovered, meaning that the oil is holding all the gas it can at the reservoir temperature and pressure, and that it is at its bubble point. Occasionally, the oil will be undersaturated. In this case, as the pressure is lowered, the pressure at which the first gas begins to evolve from the oil is defined as the bubble point. In the petroleum industry, if bubble-point pressure value is mentioned without reference to a particular temperature, the temperature is implicitly assumed to be the reservoir temperature.

As used herein, "reservoir T" or "reservoir P" or "reservoir TP" or "RTP" refer to reservoir temperature, reservoir pressure, or reservoir temperature and pressure conditions at the depth the hydrocarbon is found at. If the depth of the play is significant, an average RTP within the play can be used.

As used herein, "standard TP" or "STP" is defined as a temperature of 273.15 K (0° C., 32° F.) and an absolute pressure of exactly 105 Pa (100 kPa, 1 bar). Standard temperature and pressure in the oil industry may vary, however, as standard temperature is 15° C. and pressure may vary by state regulations. Further, many use ambient conditions in the lab instead as providing for easier experiments.

As used herein, "saturation pressure" is the pressure at a given temperature where the fluid goes into the two-phase region (from a one-phase region). The two-phase region may be influenced by gas concentration and oil composition at a given reservoir temperature and pressure. The vapor pressure of a liquid can be defined as the saturation pressure at ambient temperature. Inversely, the saturation pressure of a gas condensate is its dewpoint pressure. Saturation pressure is equivalent to bubble point pressure at a given pressure and temperature below the critical point. At temperatures above the critical point, the saturation pressure is equivalent to dew point until a single phase gas reservoir is reached at an upper temperature.

As used herein, "zero-flash" refers to flashing a live oil sample to standard conditions in a closed loop system so that nothing escapes.

The use of the word "a" or "an" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

Any claim or claim element introduced with the open transition term "comprising," may also be narrowed to use the phrases "consisting essentially of" or "consisting of," and vice versa. However, the entirety of claim language is not repeated verbatim in the interest of brevity herein.

The following abbreviations may be used herein:

| ABBREVIATION | TERM |
| --- | --- |
| API | American Petroleum Institute |
| BHP | bottom-hole pressure |
| CCE | Constant composition expansion, aka constant mass expansion (CME). The bubble point pressure is determined by an experiment called the CCE. The device used to perform this experiment is the PVT cell. CCE test is performed on a sample in a high pressure cell fitted with a glass window. In this test the cell pressure is reduced in steps and the pressure at which the first sign of gas bubbles is observed is recorded as bubble-point pressure for the oil samples and the first sign of liquid droplets is recorded as the dew-point pressure for the gas condensate samples. |
| FC-40 | a commercial inert fluid used to store cores, also known as FLUORINERT ™ Not actually inert as it dissolves lighter hydrocarbons. |
| FID | Flame Ionization detector |
| GC | Gas chromatography |
| GOR | Gas to oil ratio |
| GTM | Gas transient model |
| HPHT | High pressure, high temperature—suitable for RTP conditions. |
| HPLC | High pressure liquid chromatography |
| P | Pressure |
| RTP | Reservoir Temperature & Pressure |
| STP | Standard Temperature & Pressure |
| TAN | Total acid number |
| TP | Temperature & Pressure |
| T | Temperature |
| PVT cell | A pressure, volume, temperature cell—a vessel capable of assay at RTP. |

BRIEF DESCRIPTION OF THE DRAWINGS

FIG. 1.1. CCE experiment on live oil at 303° F. Relative volume as a function of pressure.

FIG. 1.2. CCE experiment on live oil at 303° F. Oil compressibility as a function of pressure.

FIG. 2.1. CCE experiment of live oil/FC-40 fluid system at 303° F. Relative volume as a function of pressure.

FIG. 2.2. CCE experiment of live oil/FC-40 fluid system at 303° F. Oil/FC-40 compressibility as a function of pressure.

Figure 5:
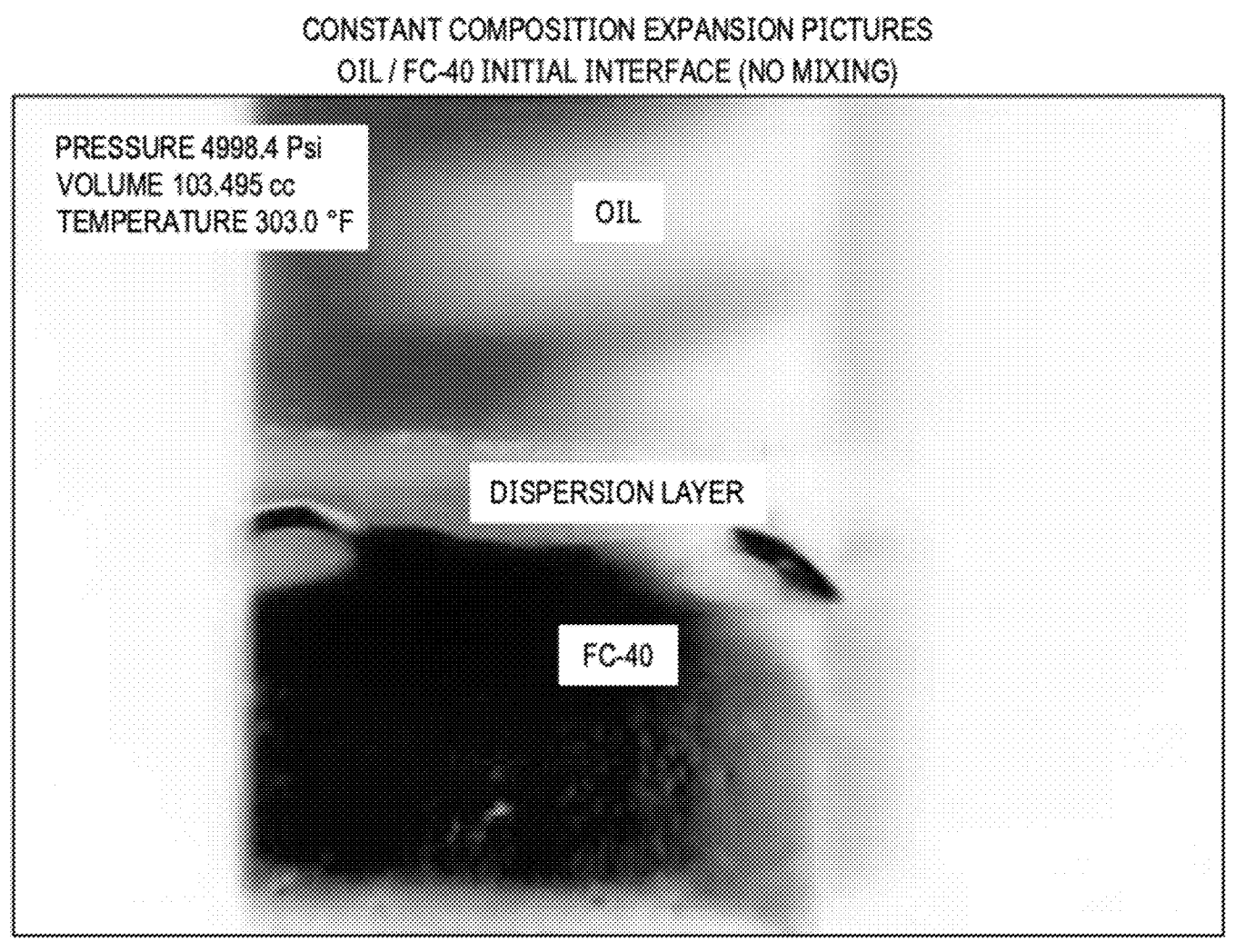

FIG. 5. PICTURE 3: Oil/FC-40 initial interface (no mixing).

Figure 7:
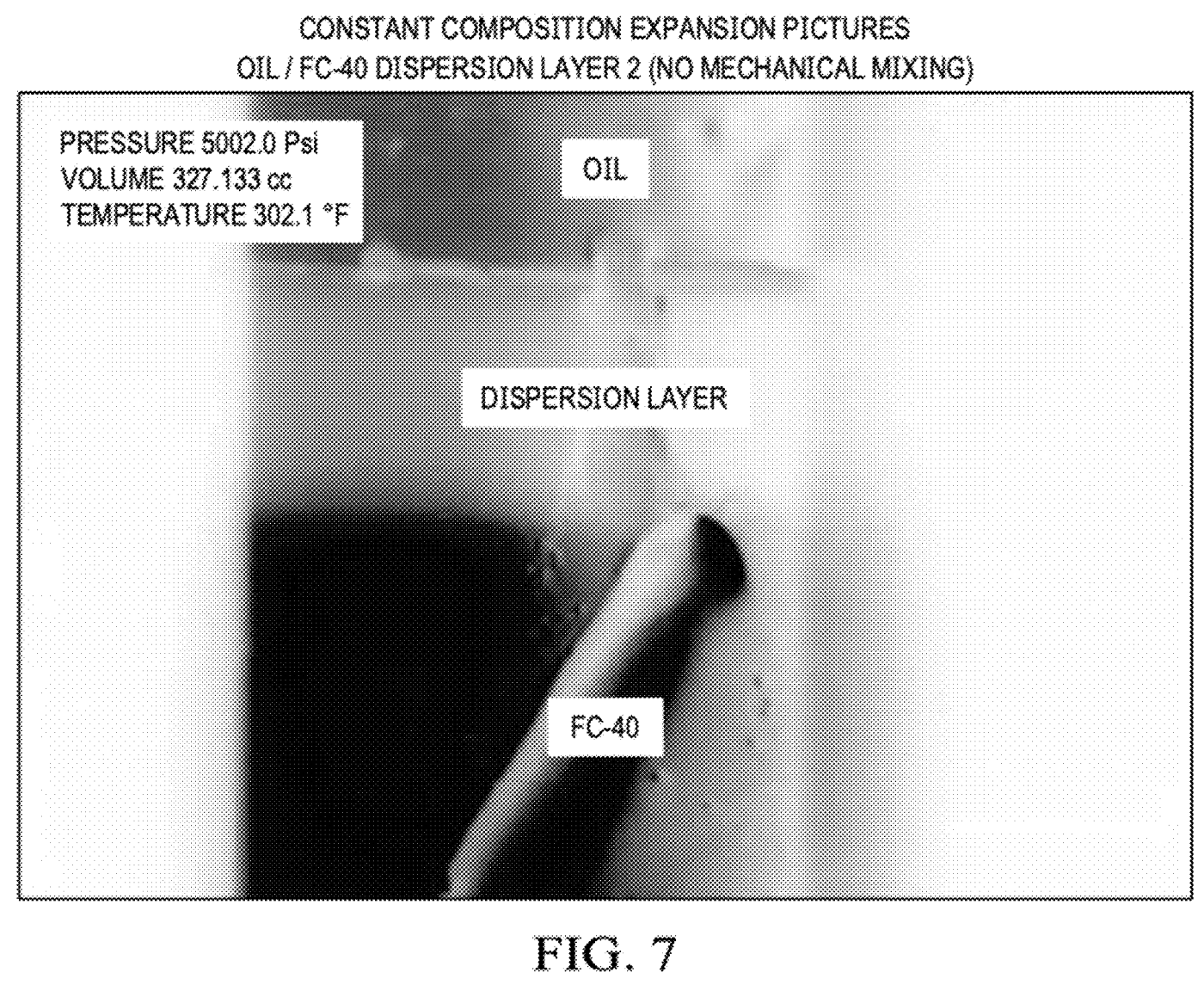

FIG. 7. PICTURE 5: Oil/FC-40 dispersion layer 2 (no mechanical mixing).

FIG. 9. PICTURE 7: Oil/FC-40 interface fluid change during mechanical mixing.

FIG. 11. PICTURE 9: Oil/FC-40 interface at saturation pressure.

DETAILED DESCRIPTION OF THE DISCLOSURE

Figure 3:
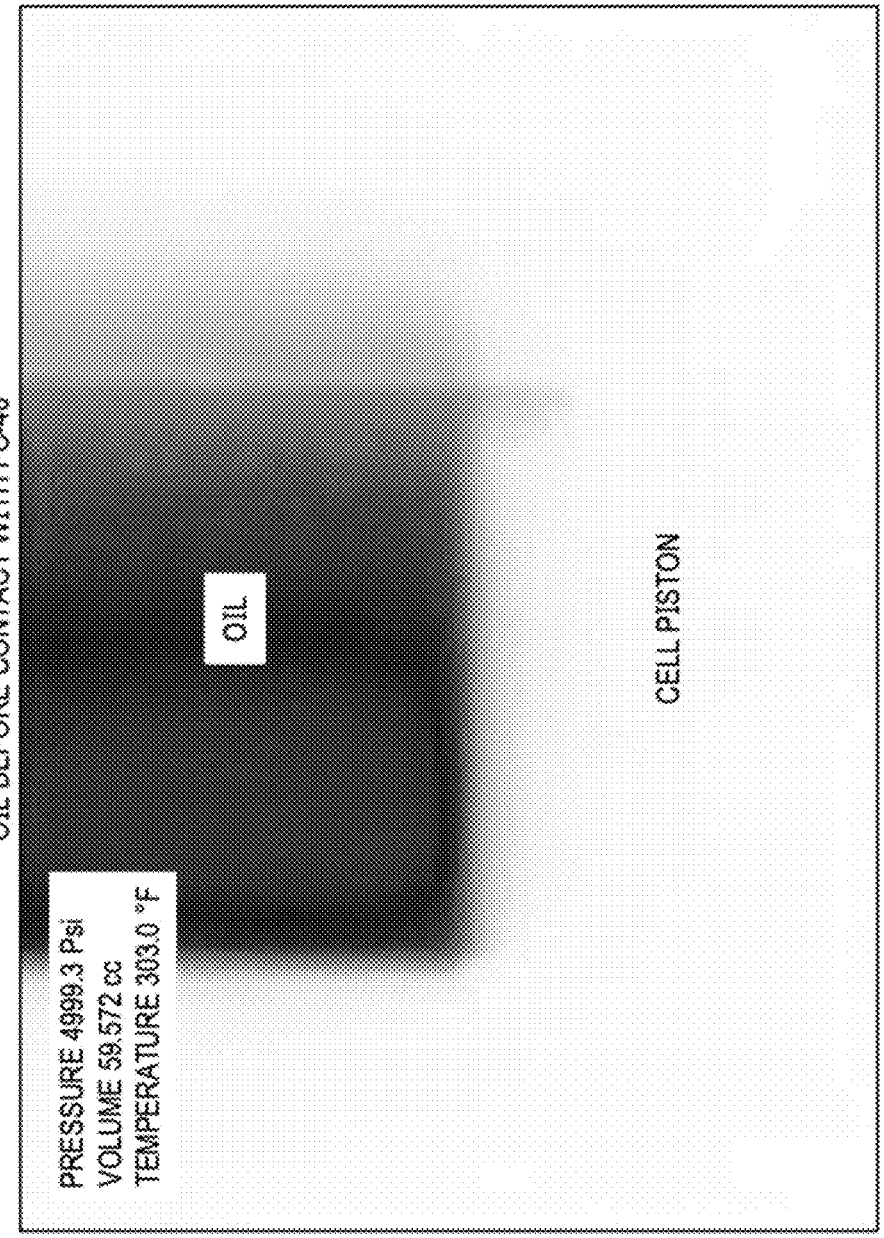
FIG. 3. PICTURE 1: Oil before contact with FC-40.
Figure 4:
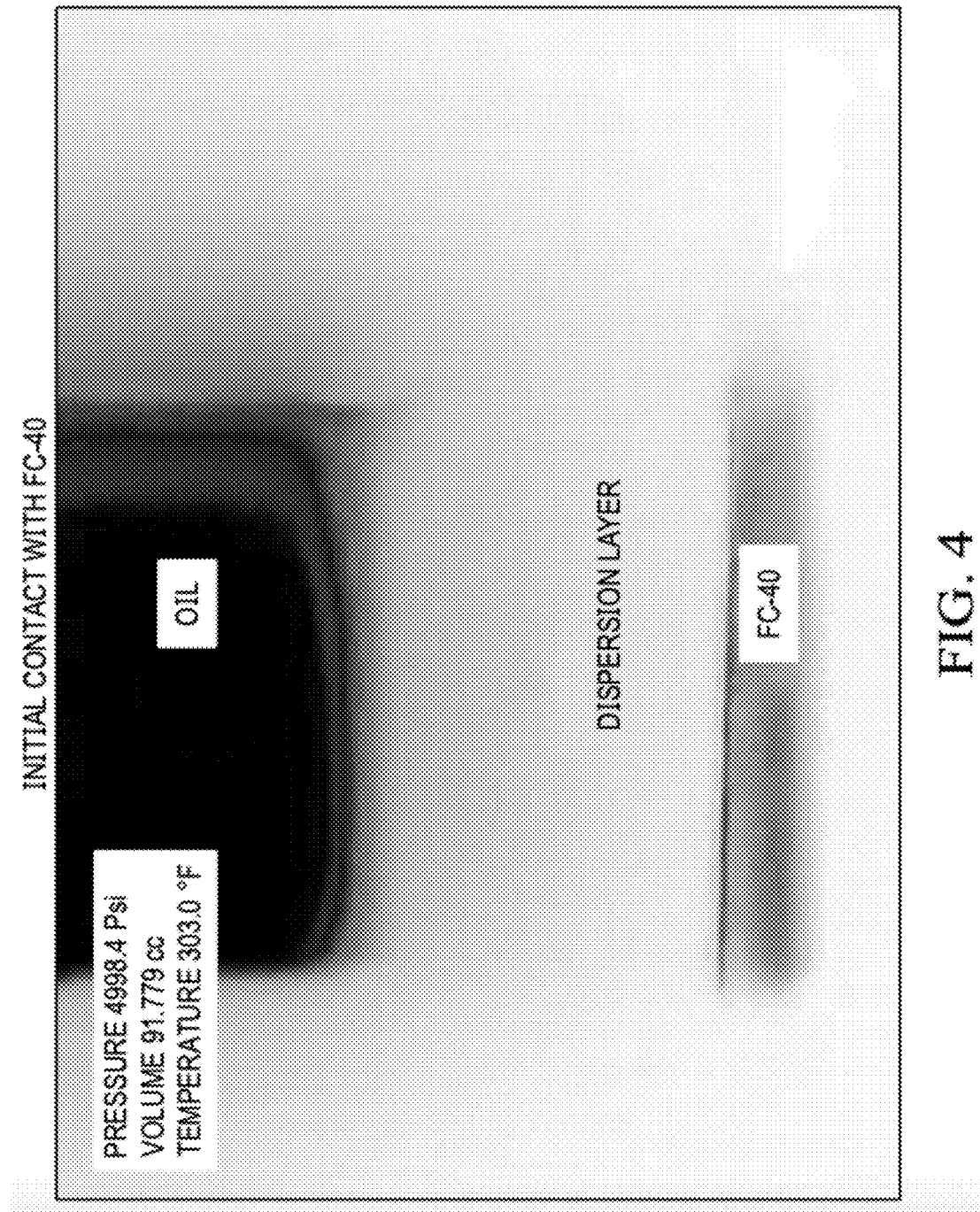
FIG. 4. PICTURE 2: Initial contact with FC-40.
Figure 6:
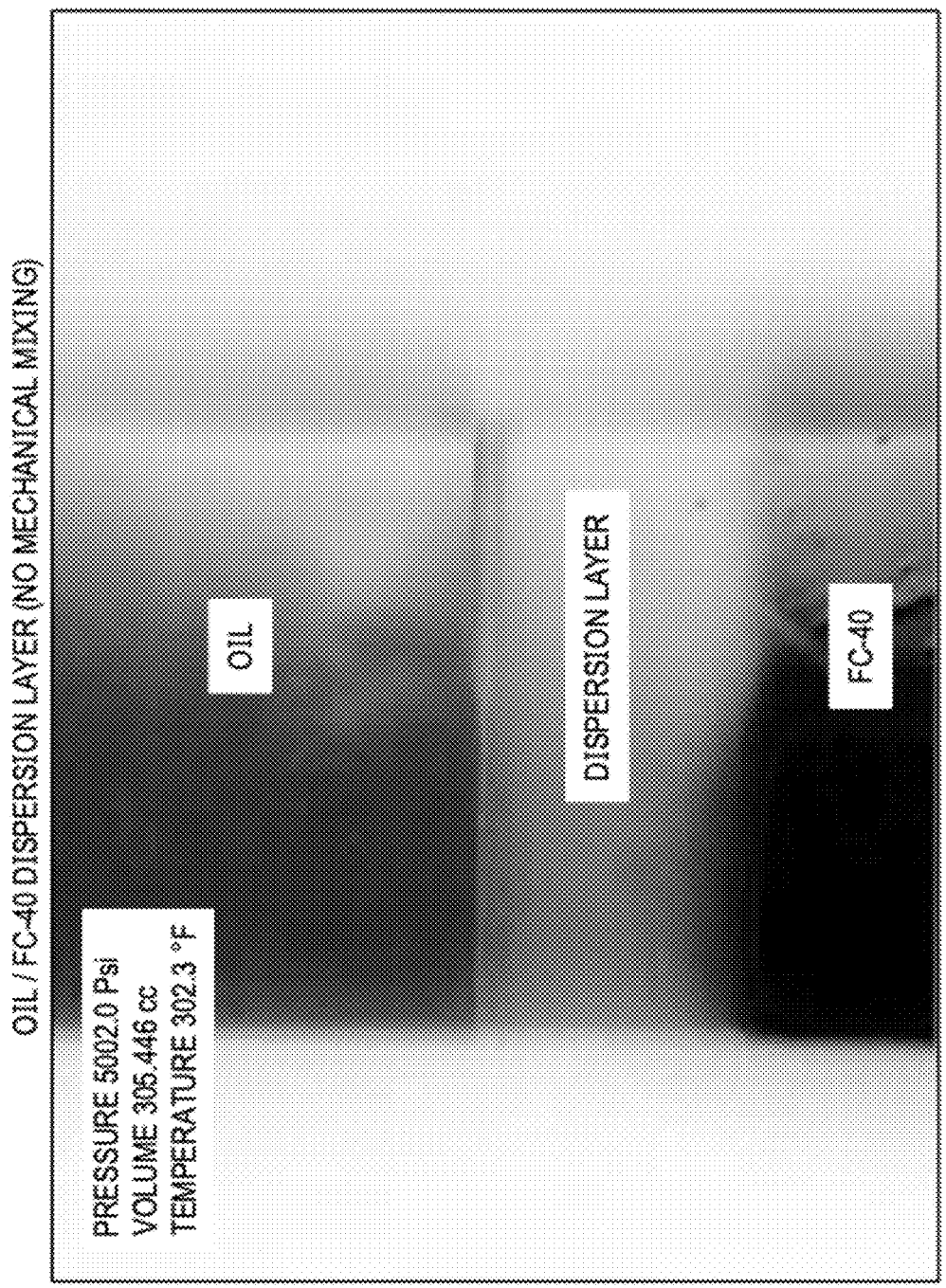
FIG. 6. PICTURE 4: Oil/FC-40 dispersion layer (no mechanical mixing).
Figure 8:
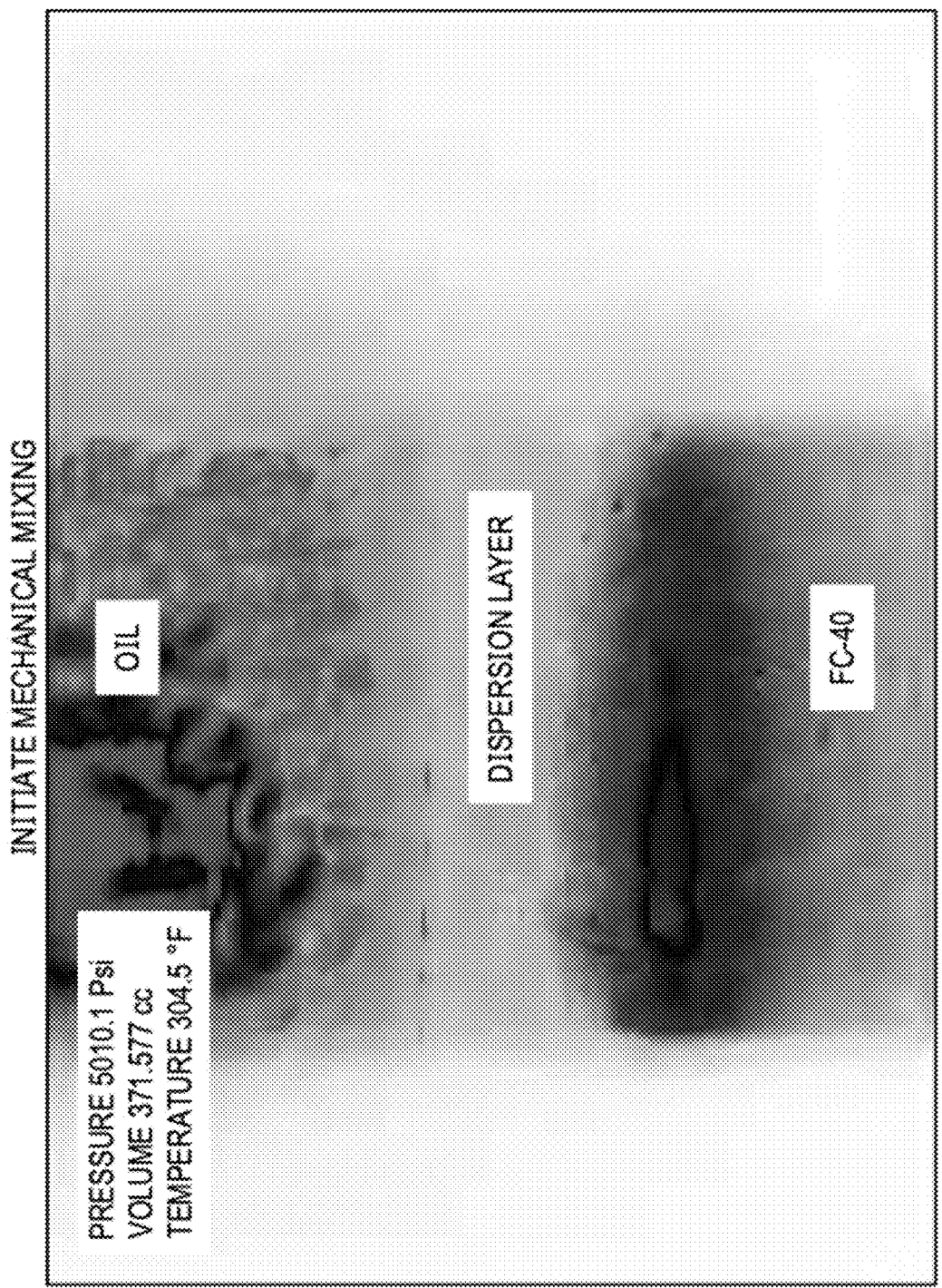
FIG. 8. PICTURE 6: Initiate mechanical mixing.
Figure 10:
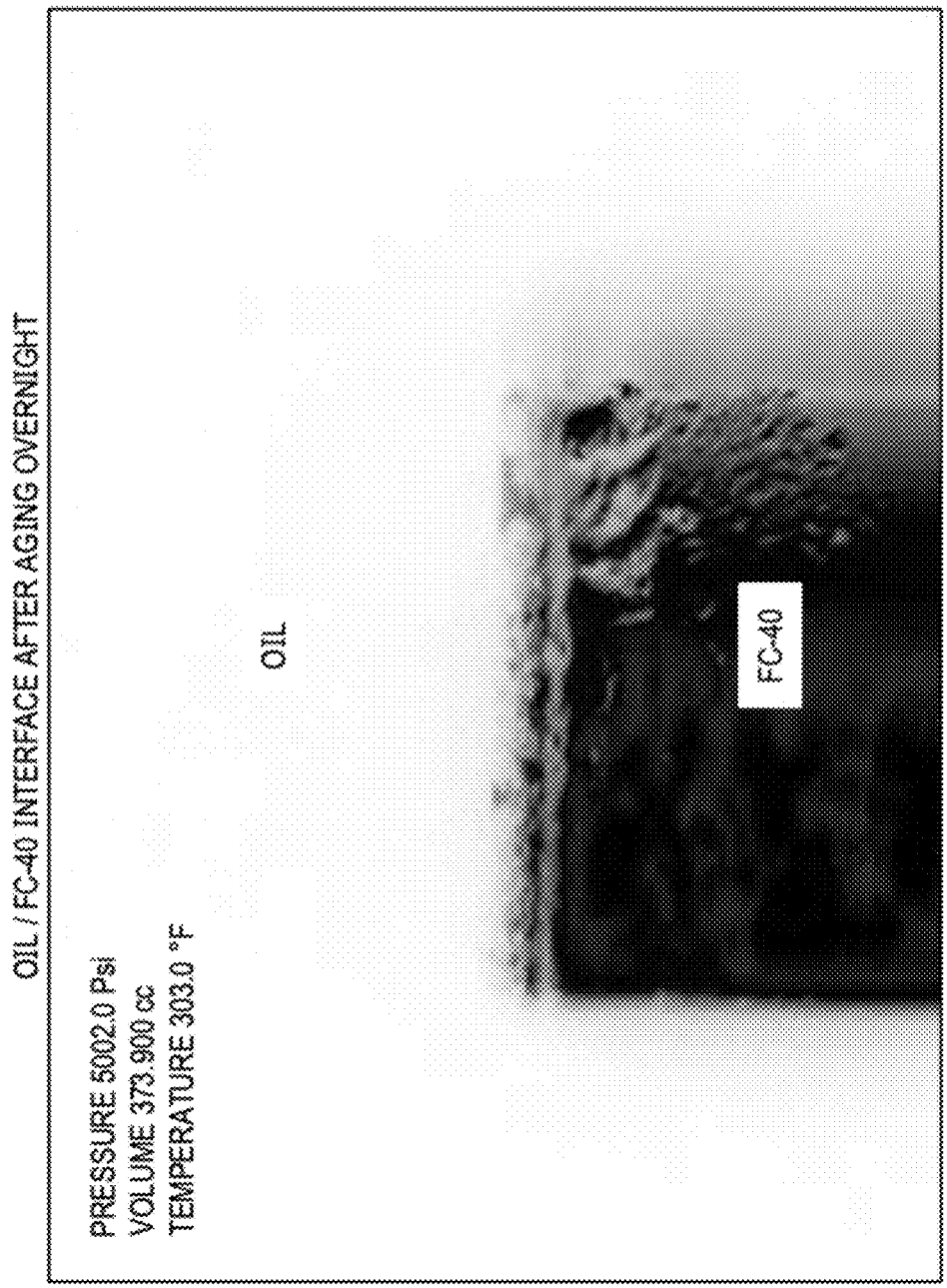
FIG. 10. PICTURE 8: Oil/FC-40 interface after aging overnight.
Figure 12:
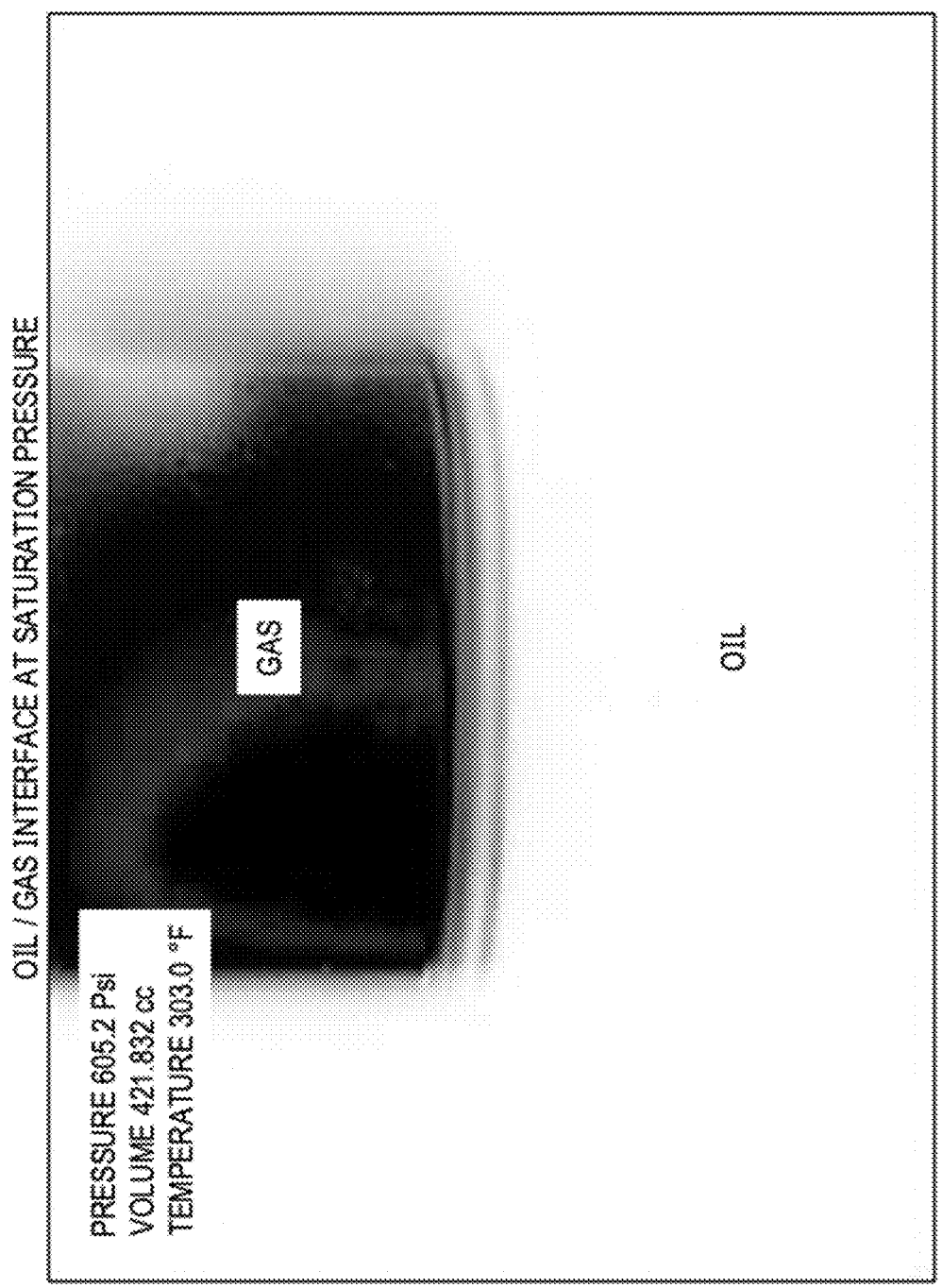
FIG. 12. PICTURE 10: Oil/gas interface at saturation pressure.

To further advance our sealed cell development work, an experiment was devised to understand liquid and gas phase hydrocarbon solubilities in FC-40 (FLUORINERT™). Previous accepted industry standards for oil solubilities in FC-40 (e.g., none) were established at atmospheric temperature and pressure conditions. However, due to the nature of the sealed cell acquisition and laboratory procedures, FC-40, reservoir samples and associated hydrocarbons are in contact with each other at pressures and temperatures in great excess of those used to establish the original solubility standards. Thus, we suspected that the prior data is not accurate.

To understand the temperature and pressure impact on hydrocarbon solubilities in FC-40 a number of tests at RTP were conducted, as described below. In these experiments, Eagle Ford Hunsaker B9 live oil samples with reconditioned FC-40 fluid were studied at RTP of this play (5000 psia, 303° F.). In general, the live oil is characterized before and after equilibration with FC-540 or other test fluid, and changes in the characterization indicate that the test fluid is not inert. In particular, one might see changes in density, components, bubble point, dew point and the like. In this instance, we determined that FC-40 is not inert—solubilizing some of the lighter oil components and thus changing each of these parameters.

It is common to use recycled FC-40 in the coring apparatus due to the high expense of FC-40 and in reliance on the assumption that it is inert. Depending on the program, we have requested virgin FC-40 to be used, but our initial proof of concept work was performed with used FC-40. Preparing the FC-40 as described herein ensures if the experiment is undertaken with recycled fluids the full solubility of oil in the FC-40 is measured.

FC-40 fluid obtained from previous pressure core projects was subjected to vacuum and heat overnight to remove any previously solubilized hydrocarbon components. The FC-40 fluids from different core samples were combined and then analyzed for chemical constituency with gas chromatography with carbon disulfide ($CS_2$) solvent with an internal standard.

To obtain the composition of live oil, we flash to ambient conditions, measure the gas, the dead oil composition, and the gas to oil ratio (GOR) and calculate the live oil composition from that by adding the gas components back in. The same can be done after equilibration of test fluid, such as FC-40, at RTP and the results compared to determine if the test fluid is indeed inert.

The bubble point pressure is determined by an experiment called the constant composition expansion or CCE. The CCE is done on the live oil before and after RTP equilibration with FC-40. If FC-40 is truly inert, the bubble point should not change. To perform a CCE, a known volume of live oil from a cylinder is transferred to a PVT cell. The live oil or live oil and FC-40 mixture are stabilized for 24 hours at RTP conditions. Then, an isothermal depressurization of at least 9 pressure steps is undertaken above saturation pressure. Below the bubble point pressure, a similar isothermal depressurization down to maximum expansion of the PVT cell volume is conducted. Cell volume is recorded at each pressure step. Saturation pressure is determined visually (herein we used bubble point) and graphically from the CCE experiment.

In more detail, these experiments are described as follows:

Fc-40 and Live Oil Mixture Study

The following experimental procedures were followed, and corresponding results are included herein:
1. Measure the composition of live oil (including weight % of the components) and density (HPHT densitometer) at 5000 psi and 303° F. (RTP).
2. Perform a CCE test to determine bubble point of live oil at RTP.
3. Flash the live oil and measure the density of the remaining oil.
4. Clean the cell and charge it with 310 cc of reconditioned FC-40 and 60-cc live oil.
5. Mix.
6. Equilibrate the mixture at RTP.
7. Measure the volume of the oil phase and FC-40 phase at RTP.
8. Perform another CCE experiment to determine bubble point of the equilibrated FC-40/oil system at RTP.
9. Displace the FC-40 and flash a portion of the remaining oil phase to STP or ambient conditions to measure amount and composition of gas that leaves solution.
10. Displace the remainder of the oil phase and measure density (HPHT densitometer) and composition of the oil at STP.

The reservoir fluid composition is reported in Table 1. It had a bubble point of 3547 psia at 303° F. (Table 2). Constant composition expansion at 303° F. indicated a fluid density of 0.5302 g/cc at the saturation pressure (bubble point) of 3547 psia (Table 3), and average total compressibility of $4.227 \times 10^{-5}$ $psi^{-1}$ (Table 4). Table 5 reports a constant composition expansion experiment performed on the reservoir fluid/FC-40 mix where a bubble point of 617 psia (shown in Table 6) at 303° F. was measured. The oil phase volume shrank from 60 cc at 5015 psig to 20.30 cc after mixing. FIG. 4-7 (Pictures 2-5) show the rapid diffusion of the oil into the FC-40 phase before mixing.

The 20.3 cc of oil remaining was displaced and its composition measured as reported in Table 7. The FC-40 was displaced and flashed to ambient conditions; a gas phase was recovered and its composition measured and an oil phase that separated from the FC-40 also had its composition determined.

Figure 13:
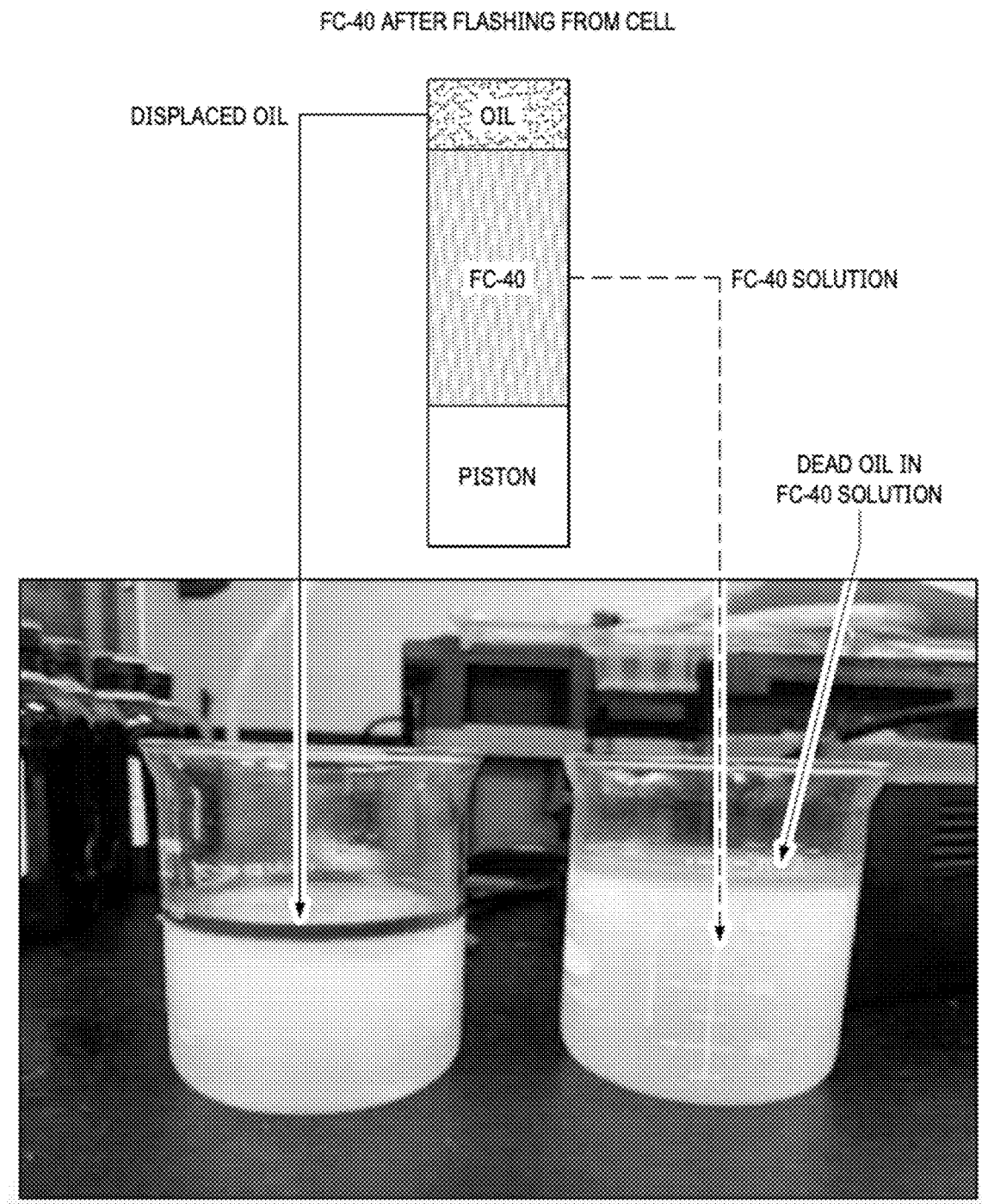
FIG. 13. PICTURE 11: FC-40 after flashing from cell.

The composition of the oil components that solubilized into the FC-40 was estimated in Table 8 by combining the gas and oil phases that came out of the FC-40 at ambient conditions by material balance. The material balance around the entire experiment (Table 9) indicates that the live oil composition reported in Table 8 should have more light ends. This is probably due to the fact that light hydrocarbons have significant solubility in FC-40 even at atmospheric conditions. FIG. 13 confirms that the light hydrocarbons are more soluble in FC-40, leaving the heavier components in the oil phase.

Since the current standard so-called "inert" fluid (FC-40) (Table 10) removes light hydrocarbons, it would be beneficial to find a better inert fluid for downhole uses at RTP. The ideal fluid should be dense, and inert to hydrocarbons, as well as not preferentially solubilize any of the hydrocarbon components. In addition, the solution should be reasonably safe to use, and not contribute to environmental degradation or present safety hazards.

To that end, we will test silicon-based molecules that are fully substituted with fluorine, or silicon-based compounds with hydrophobic R groups, including siloxanes ($SiH_3(OSiH_2)nOSiH_3$), or silicones.

Silicone fluids can be discussed in two categories: inert fluids and functional fluids. Polydialkyl-, arylalkyl- and fluoroalkylsiloxane polymers and co-polymers, carrying no reactive (under-the-use conditions) groups, belong to the first category and may be tested as described herein.

A possible test fluid is $(CH_3)_3$—Si—O—$Si(CH_3)_2$—O—$Si(CH_3)(R)$—O—$Si(CH_3)_3$ where (R) is hydrophobic.

Another test fluid might be a fluorosyl:

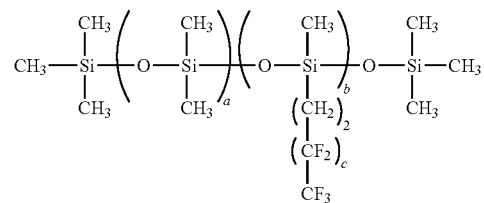

where c = 2-5

In fact, many fluorosyls are available for testing herein, including Fluorosil 2010, Fluorosil H418, Fluorosil J15, Fluorosil L118, Fluorosil OH C7-F, Silwax F, Fluorosil OH ACR C7-F, Fluorosil TFP 1000, Fluorosil TFP 10,000, Fluorosil TFP D7, and the like.

High Temperature Silicones such as Dynalene 600 or SYLTHERM (a polydimethylsiloxane liquid) may also be tested.

Another option is phenylsiloxane-dimethylsiloxane copolymer and diphenylsiloxane-dimethylsiloxane copolymers. As phenyl groups replace methyl groups in a polysiloxane, several changes occur. Oxidation resistance, thermal stability, and shear resistance are enhanced.

Modified silicones that have a higher density and chemical resistance and are potential candidates include:

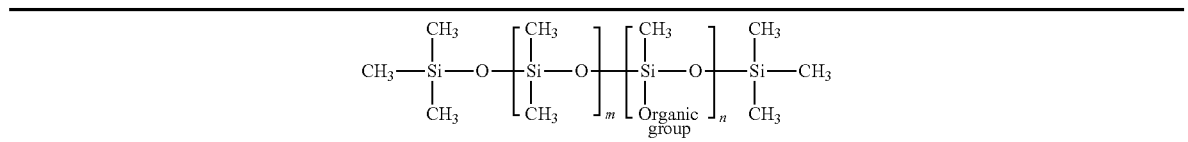

| Modifcation type | Organic group | Product name | Viscosity (25° C.) [mm/s] | Specific gravity (25° C.) | Refractive Index (25° C.) | Features |
|---|---|---|---|---|---|---|
| Fluoroalkyl | —$CH_2CH_2CF_3$ | FL-5 | 120 | 0.99 | 1.400 | Good lubricity |
| | | X-22-821 | 120 | 1.09 | 1.390 | Chemical |
| | | X-22-822 | 100 | 1.15 | 1.384 | resistance |
| | | FL-100-100cs | 100 | 1.23 | 1.379 | Oil & |
| | | FL-100-450cs | 450 | 1.28 | 1.381 | solvent |
| | | FL-100-1,000cs | 1,000 | 1.28 | 1.381 | resistance |
| | | FL-100-10,000cs | 10,000 | 1.30 | 1.382 | High specific gravity Poor solubility Good releasability |

Polyether-modified

| Modifcation type | Organic group | Product Name | Viscosity (25° C.) [mm/s] | Specific gravity (25° C.) | Refractive index (25°C.) | HLB | Features |
|---|---|---|---|---|---|---|---|
| Polyether | —$R(C_2H_4O)_a(C_3H_6O)_bR'$ | KF-351A | 70 | 1.06 | 1,450 | 12 | Water |
| | | KF-352A | 1,600 | 1.03 | 1,446 | 7 | soluble |
| | | KF-353 | 430 | 1.04 | 1,438 | 10 | Water |
| | | KF-354L | 200 | 1.10 | 1,463 | 16 | dispersible |
| | | KF-355A | 150 | 1.07 | 1,453 | 12 | Easily |
| | | KF-615A | 920 | 1.05 | 1,451 | 10 | emulsifable |
| | | KF-945 | 130 | 1.00 | 1,420 | 4 | Low |
| | | KF-640 | 20 | 1.01 | 1,444 | 14 | surface |
| | | KF-642 | 50 | 1.04 | 1,443 | 12 | tension |
| | | KF-643 | 19 | 1.01 | 1,442 | 14 | Good |
| | | KF-644 | 38 | 1.02 | 1,446 | 11 | permeability |
| | | KF-6020 | 180 | 1.00 | 1,417 | 4 | Anti- |
| | | KF-6204 | 70 | 1.05 | 1,451 | 10 | fogging |
| | | X-22-4515 | 4,000 | 1.03 | 1,445 | 5 | property |

-continued $$CH_3-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_m-\left[\underset{\underset{\text{Organic group}}{|}}{\overset{\overset{CH_3}{|}}{Si}}-O\right]_n-\underset{\underset{CH_3}{|}}{\overset{\overset{CH_3}{|}}{Si}}-CH_3$$

| | | | | | | | |
|---|---|---|---|---|---|---|---|
| Polyether (odortest) | —R(C₂H₄O)ₐ(C₃H₆O)ᵦR' | | KF-6011 | 130 | 1.07 | 1,450 | 12 | Compatibility |
| | | | KF-6012 | 1,500 | 1.03 | 1,448 | 7 | |
| | | | KF-6015 | 130 | 1.00 | 1,419 | 5 | |
| | | | KF-6017 | 530 | 1.01 | 1,420 | 5 | |

Phenyl-modified

| Modification type | Organic group | Product name | Viscosity (25° C.) [mm/s] | Specific gravity (25° C.) | Refractive index (25° C.) | Features |
|---|---|---|---|---|---|---|
| Phenyl | $CH_3-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_m-\left[\underset{\underset{C_6H_5}{|}}{\overset{\overset{C_6H_5}{|}}{Si}}-O\right]_n-\underset{\underset{CH_3}{|}}{\overset{\overset{CH_3}{|}}{Si}}-CH_3$ | KF-50-100cs | 100 | 0.995 | 1.427 | Heat resistance |
| | | KF-50-300cs | 300 | 0.996 | 1.427 | |
| | | KF-50-1,000cs | 1,000 | 1.00 | 1.427 | High refractive index |
| | | KF-50-3,000cs | 3,000 | 1.00 | 1.427 | |
| | | KF-53 | 170 | 1.06 | 1.485 | Compatibility |
| | | KF-54 | 400 | 1.07 | 1.505 | Low-temperature resistance |
| | | X-21-3265 | 400 | 1.07 | 1.505 | |
| | | KF-54SS | 500 | 1.07 | 1.504 | |

Brominated hydrocarbons may also work, and mercury compounds or mercury containing mixes in the manner similar to that described herein. Any of the above described or similar compounds that test as inert in the herein described tests will be used as core sampling inert fluids and/or core storage inert fluids.

Suitable compounds may not be 100% inert, but the ideal solution would be 95% inert or better for the time it takes to collect core samples and test them—e.g., no more than 5% change in content. Thus, the inert fluid should be at least 95% inert when tested with core at RTP for at least 6 hours, preferably at least 12, or even 24, 36 or 48 hours. Even more preferred is a 96, 97, 98, or 99% inertness.

TABLE 1

Reservoir Fluid Composition

| Component | | Flashed Gas Mole % | Flashed Oil Mole % | Flashed Oil Wt % | Molecular Weight | Specific Gravity | Reservoir Fluid Mole % | Reservoir Fluid Wt % |
|---|---|---|---|---|---|---|---|---|
| Nitrogen | $N_2$ | 0.237 | 0.000 | 0.000 | 28.01 | 0.8100 | 0.171 | 0.067 |
| Carbon Dioxide | $CO_2$ | 1.028 | 0.000 | 0.000 | 44.01 | 0.8270 | 0.741 | 0.458 |
| Hydrogen Sulphide | $H_2S$ | 0.000 | 0.000 | 0.000 | 34.08 | 0.7960 | 0.000 | 0.000 |
| Methane | $C_1$ | 68.722 | 0.074 | 0.006 | 16.05 | 0.3000 | 49.593 | 11.181 |
| Ethane | $C_2$ | 14.516 | 0.325 | 0.051 | 30.07 | 0.3560 | 10.562 | 4.461 |
| Propane | $C_3$ | 8.004 | 0.701 | 0.161 | 44.10 | 0.5010 | 5.969 | 3.698 |
| i-Butane | $i\text{-}C_4$ | 1.340 | 0.326 | 0.099 | 58.12 | 0.5570 | 1.057 | 0.863 |
| n-Butane | $n\text{-}C_4$ | 2.879 | 1.365 | 0.413 | 58.12 | 0.5790 | 2.457 | 2.006 |
| i-Pentane | $i\text{-}C_5$ | 1.190 | 1.426 | 0.535 | 72.15 | 0.6200 | 1.256 | 1.273 |
| n-Pentane | $n\text{-}C_5$ | 0.990 | 2.217 | 0.832 | 72.15 | 0.6260 | 1.332 | 1.350 |
| Hexanes | $C_6$ | 0.708 | 5.727 | 2.504 | 84.00 | 0.6900 | 2.106 | 2.486 |
| Heptanes | $C_7$ | 0.182 | 8.002 | 3.957 | 95.00 | 0.7270 | 2.361 | 3.151 |
| Octanes | $C_8$ | 0.106 | 10.632 | 5.921 | 107.00 | 0.7490 | 3.039 | 4.568 |
| Nonanes | $C_9$ | 0.091 | 9.451 | 5.952 | 121.00 | 0.7680 | 2.699 | 4.588 |
| Decanes | $C_{10}$ | 0.007 | 7.451 | 5.274 | 136.00 | 0.7820 | 2.081 | 3.977 |
| Undecanes | $C_{11}$ | 0.000 | 5.945 | 4.611 | 149.00 | 0.7930 | 1.657 | 3.467 |
| Dodecanes | $C_{12}$ | 0.000 | 4.796 | 4.069 | 163.00 | 0.8040 | 1.337 | 3.060 |
| Tridecanes | $C_{13}$ | | 4.593 | 4.207 | 176.00 | 0.8150 | 1.280 | 3.164 |
| Tetradecanes | $C_{14}$ | | 3.952 | 3.929 | 191.00 | 0.8260 | 1.101 | 2.955 |
| Pentadecanes | $C_{15}$ | | 3.579 | 3.856 | 207.00 | 0.8360 | 0.997 | 2.900 |
| Hexadecanes | $C_{16}$ | | 2.906 | 3.343 | 221.00 | 0.8430 | 0.810 | 2.514 |
| Heptadecanes | $C_{17}$ | | 2.617 | 3.228 | 237.00 | 0.8510 | 0.729 | 2.428 |
| Octadecanes | $C_{18}$ | | 2.468 | 3.199 | 249.00 | 0.8560 | 0.688 | 2.406 |
| Nonadecanes | $C_{19}$ | | 2.301 | 3.125 | 261.00 | 0.8610 | 0.641 | 2.350 |
| Eicosanes | $C_{20}$ | | 1.897 | 2.715 | 275.00 | 0.8660 | 0.529 | 2.042 |
| Heneicosanes | $C_{21}$ | | 1.718 | 2.584 | 289.00 | 0.8710 | 0.479 | 1.943 |
| Docosanes | $C_{22}$ | | 1.485 | 2.342 | 303.00 | 0.8760 | 0.414 | 1.761 |
| Tricosanes | $C_{23}$ | | 1.354 | 2.234 | 317.00 | 0.8810 | 0.377 | 1.680 |
| Tetracosanes | $C_{24}$ | | 1.220 | 2.102 | 331.00 | 0.8850 | 0.340 | 1.581 |
| Pentacosanes | $C_{25}$ | | 1.086 | 1.949 | 345.00 | 0.8880 | 0.302 | 1.466 |
| Hexacosanes | $C_{26}$ | | 1.011 | 1.890 | 359.00 | 0.8920 | 0.282 | 1.421 |

TABLE 1-continued

| | | | | | | | |
|---|---|---|---|---|---|---|---|
| Heptacosanes | $C_{27}$ | 0.914 | 1.775 | 373.00 | 0.8960 | 0.255 | 1.335 |
| Octacosanes | $C_{28}$ | 0.834 | 1.680 | 387.00 | 0.8990 | 0.232 | 1.264 |
| Nonacosanes | $C_{29}$ | 0.750 | 1.562 | 400.00 | 0.9020 | 0.209 | 1.174 |
| Tricontanes | $C_{30}$ | 0.665 | 1.436 | 415.00 | 0.9050 | 0.185 | 1.080 |
| Hentriacontanes | $C_{31}$ | 0.579 | 1.292 | 429.00 | 0.9090 | 0.161 | 0.972 |
| Dotriacontanes | $C_{32}$ | 0.550 | 1.269 | 443.00 | 0.9120 | 0.153 | 0.955 |
| Tritriacontanes | $C_{33}$ | 0.499 | 1.187 | 457.00 | 0.9150 | 0.139 | 0.893 |
| Tetratriacontanes | $C_{34}$ | 0.488 | 1.197 | 471.00 | 0.9170 | 0.136 | 0.900 |
| Pentatriacontanes | $C_{35}$ | 0.404 | 1.020 | 485.00 | 0.9200 | 0.113 | 0.767 |
| Hexatriacontanes plus | C36+ | 3.693 | 12.494 | 650.00 | 0.9913 | 1.029 | 9.396 |
| | | 100.00 | 100.00 | | | 100.00 | 100.00 |
| Molecular Weight | | 24.47 | 192.13 | | | | 71.19 |

Compositional Grouping and Plus Fraction Properties

| Group | Mol % | wt % | MW | Density |
|---|---|---|---|---|
| C7+ | 24.76 | 72.16 | 207.49 | 0.8461 |
| C12+ | 12.92 | 52.41 | 255.79 | 0.8758 |
| C20+ | 5.34 | 30.63 | 408.67 | 0.9195 |
| C30+ | 1.92 | 14.96 | 555.73 | 0.9605 |
| C36+ | 1.03 | 9.40 | 650.00 | 0.9913 |

TABLE 2

Main PVT Results

TEST CONDITIONS

| | |
|---|---|
| Pressure | 5000 psia |
| Temperature | 303.0 F. |

CONSTANT COMPOSITION EXPANSION @ 303.0 F.

| | |
|---|---|
| Saturation Pressure (Bubble Point) | 3547.31 psia |
| Compressibility @ Saturation Pressure | 4.2274E−05 psia$^{-1}$ |

SEPARATOR FLUID FLASH TEST TO AMBIENT CONDITIONS

At Saturation Pressure

| | |
|---|---|
| Oil Formation Volume Factor | 2.0052 res.bbl/STB |
| Flash Gas-Oil Ratio | 1432.89 scf/STB |

At Tank Conditions

| | |
|---|---|
| Residual Oil Density | 0.7996 g/cm$^3$ |
| API Gravity | 45.47 |
| Measured MW | 195.30 |

Cylinder Number: 832808
Volume of oil left: 300 cc at 5000 psi and 303 F.

TABLE 3

Constant Composition Expansion @ 303.0 F.

| Pressure (psia) | RelativeVolume [1] | Y-Fuaction [2] | Fluid Density (g/cc) [3] | Liquid Volume Vliq/Vb % |
|---|---|---|---|---|
| 7015 | 0.9059 | | 0.5853 | |
| 6515 | 0.9146 | | 0.5797 | |
| 6015 | 0.9244 | | 0.5736 | |
| 5515 | 0.9354 | | 0.5668 | |
| 5015 | 0.3480 | | 0.5593 | |
| 4515 | 0.9627 | | 0.5598 | |
| 4015 | 0.9862 | | 0.5409 | |
| 3547 Psat | 1.0000 | | 0.5302 | 100.000 |
| 3379 | 1.0251 | 1.9791 | | 94.430 |
| 3211 | 1.6541 | 1.9339 | | 90.836 |
| 3043 | 1.0877 | 1.8886 | | 88.819 |
| 2875 | 1.1268 | 1.8434 | | 85.321 |
| 2707 | 1.1725 | 1.7982 | | 82.849 |
| 2539 | 1.2265 | 1.7530 | | 89.754 |
| 2371 | 1.2964 | 1.7077 | | 78.589 |
| 2293 | 1.3669 | 1.6625 | | 76.583 |
| 2935 | 1.4593 | 1.6173 | | 74.507 |
| 1867 | 1.5723 | 1.5721 | | 72.604 |
| 1599 | 1.7123 | 1.5268 | | 70.898 |
| 1531 | 1.8886 | 1.4816 | | 69.257 |
| 1363 | 2.1153 | 1.4364 | | 67.744 |
| 1195 | 2.4144 | 1.3912 | | 65.998 |
| 1027 | 2.8225 | 1.3459 | | 64.600 |

[1] Volume at indicated pressure per volume at saturation pressure
[2] Y Function = ((Psat − P)/P)(Relative Volume − 1)
[3] Measured by HPHT densfometer
Psat—Saturation Pressure

TABLE 4

Constant Composition Expansion @ 303.0 F.
Oil Compressibility as a Function of Pressure

| Pressure Range | | Average Total Compressibility (psi$^{-1}$) |
|---|---|---|
| From (psia) | To (psia) | |
| 7015 | 6515 | 1.903E−05 |
| 6515 | 6015 | 2.111E−05 |
| 6015 | 5515 | 2.357E−05 |
| 5515 | 5015 | 2.657E−05 |
| 5015 | 4515 | 3.049E−05 |
| 4515 | 4015 | 3.579E−05 |
| 4015 | 3547 Psat | 4.227E−05 |

TABLE 5

Constant Composition Expansion of Live Oil/FC-40 Fluid System @ 303.0 F.

| Pressure (psia) | Total Volume cc | Relative Volume [1] | Y-Function [2] | Gas Phase Volume cc | Oil Phase Volume cc |
|---|---|---|---|---|---|
| 5015 | 374.01 | 0.8822 | | | 20.30 |
| 4015 | 380.25 | 0.8969 | | | 20.61 |

TABLE 5-continued

Constant Composition Expansion of Live Oil/FC-40 Fluid System @ 303.0 F.

| Pressure (psia) | Total Volume cc | Relative Volume [1] | Y-Function [2] | Gas Phase Volume cc | Oil Phase Volume cc |
|---|---|---|---|---|---|
| 3015 | 387.90 | 0.9149 | | | 20.64 |
| 2515 | 392.72 | 0.9263 | | | 20.54 |
| 2015 | 398.36 | 0.9396 | | | 20.54 |
| 1515 | 405.22 | 0.9558 | | | 20.59 |
| 1015 | 414.00 | 0.9765 | | | 20.67 |
| 617 Psat | 423.96 | 1.0000 | | 0.0000 | 20.05 |
| 606 | 427.51 | 1.0084 | 2.165 | 6.444 | 19.79 |
| 595 | 431.73 | 1.0183 | 2.017 | 9.485 | 19.51 |
| 584 | 435.99 | 1.0284 | 1.991 | 13.961 | 19.23 |
| 573 | 446.30 | 1.0385 | 1.992 | 20.549 | 18.96 |
| 562 | 445.19 | 1.0501 | 1.954 | 28.527 | 18.78 |
| 551 | 451.63 | 1.0653 | 1.835 | 33.881 | 18.86 |
| 540 | 458.16 | 1.0807 | 1.767 | 40.240 | 18.93 |
| 529 | 464.79 | 1.0963 | 1.727 | 47.793 | 19.01 |
| 516 | 471.51 | 1.1122 | 1.704 | 56.762 | 19.08 |
| 507 | 478.70 | 1.1291 | 1.680 | 63.983 | 19.29 |
| 496 | 486.12 | 1.1466 | 1.664 | 70.907 | 19.55 |
| 485 | 493.67 | 1.1644 | 1.655 | 78.580 | 19.81 |
| 474 | 501.32 | 1.1825 | 1.653 | 87.084 | 20.07 |
| 463 | 508.66 | 1.1998 | 1.665 | 95.880 | 20.00 |
| 452 | 514.58 | 1.2138 | 1.708 | 103.248 | 18.80 |

Loading Information (5000 psig & 303° F.)

| | |
|---|---|
| Reservoir Oil, cc | 60.00 |
| FC-40, cc | 314.01 |

[1] Volume at indicated pressure per volume at saturation pressure
[2] Y Function = (Psat − P)/P)/(Relative Volume − 1)
Psat—Saturation Pressure

TABLE 6

Constant Composition Expansion of Live Oil/FC-40 Fluid System @ 303.0 F. Live Oil/ FC-40 Fluid System Compressibility as a Function of Pressure

| Pressure Range | | Average Total Compressibility (psi$^{-1}$) |
|---|---|---|
| From (psia) | To (psia) | |
| 5015 | 4015 | 1.655E−05 |
| 4015 | 3015 | 1.991E−05 |
| 3015 | 2515 | 2.468E−05 |
| 2515 | 2015 | 2.854E−05 |
| 2015 | 1515 | 3.417E−05 |
| 1515 | 1015 | 4.286E−05 |
| 1015 | 617 Psat | 5.971E−05 |

TABLE 7

Displaced Oil Phase Composition (After mixing with FC-40 in the PVT cell)

| Component | | Flashed Gas Mole % | Flashed Oil Mole % | Flashed Oil Wt % | Molecular Weight | Specific Gravity | Oil Phase Mole % | Oil Phase Wt % |
|---|---|---|---|---|---|---|---|---|
| Nitrogen | $N_2$ | 2.910 | 0.000 | 0.000 | 28.01 | 0.8100 | 0.686 | 0.089 |
| Carbon Dioxide | $CO_2$ | 0.805 | 0.000 | 0.000 | 44.01 | 0.8270 | 0.190 | 0.038 |
| Hydrogen Sulphide | $H_2S$ | 0.000 | 0.000 | 0.000 | 34.08 | 0.7960 | 0.000 | 0.000 |
| Methane | $C_1$ | 66.763 | 0.015 | 0.001 | 16.05 | 0.3000 | 15.742 | 1.165 |
| Ethane | $C_2$ | 16.474 | 0.191 | 0.021 | 30.07 | 0.3560 | 4.028 | 0.559 |
| Propane | $C_3$ | 8.075 | 0.651 | 0.104 | 44.10 | 0.5010 | 2.400 | 0.488 |
| i-Butane | i-$C_4$ | 1.050 | 0.290 | 0.061 | 58.12 | 0.5570 | 0.469 | 0.126 |
| n-Butane | n-$C_4$ | 2.180 | 1.035 | 0.218 | 58.12 | 0.5790 | 1.304 | 0.350 |
| i-Pentane | i-$C_5$ | 0.603 | 0.772 | 0.201 | 72.15 | 0.6200 | 0.732 | 0.244 |
| n-Pentane | n-$C_5$ | 0.572 | 1.109 | 0.290 | 72.15 | 0.6260 | 0.983 | 0.327 |
| Hexanes | $C_6$ | 0.392 | 2.377 | 0.722 | 84.00 | 0.6900 | 1.909 | 0.739 |
| Heptanes | $C_7$ | 0.110 | 3.547 | 1.219 | 95.00 | 0.7270 | 2.737 | 1.199 |
| Octanes | $C_8$ | 0.045 | 6.466 | 2.503 | 107.00 | 0.7490 | 4.953 | 2.444 |
| Nonanes | $C_9$ | 0.018 | 4.824 | 2.111 | 121.00 | 0.7680 | 3.691 | 2.060 |
| Decanes | $C_{10}$ | 0.002 | 4.317 | 2.124 | 136.00 | 0.7820 | 3.301 | 2.070 |
| Undecanes | $C_{11}$ | 0.000 | 3.864 | 2.083 | 149.00 | 0.7930 | 2.954 | 2.029 |
| Dodecanes | $C_{12}$ | 0.000 | 3.538 | 2.086 | 163.00 | 0.8040 | 2.705 | 2.033 |
| Tridecanes | $C_{13}$ | | 3.785 | 2.410 | 176.00 | 0.8150 | 2.893 | 2.348 |
| Tetradecanes | $C_{14}$ | | 3.645 | 2.519 | 191.00 | 0.8260 | 2.786 | 2.454 |
| Pentadecanes | $C_{15}$ | | 3.675 | 2.752 | 207.00 | 0.8360 | 2.809 | 2.681 |
| Hexadecanes | $C_{16}$ | | 3.332 | 2.664 | 221.00 | 0.8430 | 2.547 | 2.596 |
| Heptadecanes | $C_{17}$ | | 3.256 | 2.791 | 237.00 | 0.8510 | 2.488 | 2.720 |
| Octadecanes | $C_{18}$ | | 3.275 | 2.950 | 249.00 | 0.8560 | 2.504 | 2.875 |
| Nonadecanes | $C_{19}$ | | 3.338 | 3.152 | 261.00 | 0.8610 | 2.552 | 3.071 |
| Eicosanes | $C_{20}$ | | 2.984 | 2.969 | 275.00 | 0.8660 | 2.281 | 2.893 |
| Heneicosanes | $C_{21}$ | | 2.884 | 2.584 | 289.00 | 0.8710 | 2.205 | 2.938 |
| Docosanes | $C_{22}$ | | 2.655 | 2.910 | 303.00 | 0.8760 | 2.029 | 2.835 |
| Tricosanes | $C_{23}$ | | 2.556 | 2.931 | 317.00 | 0.8810 | 1.954 | 2.856 |
| Tetracosanes | $C_{24}$ | | 2.422 | 2.900 | 331.00 | 0.8850 | 1.852 | 2.826 |
| Pentacosanes | $C_{25}$ | | 2.252 | 2.811 | 345.00 | 0.8880 | 1.722 | 2.739 |
| Hexacosanes | $C_{26}$ | | 2.186 | 2.839 | 359.00 | 0.8920 | 1.671 | 2.766 |

TABLE 7-continued

| | | | | | | | |
|---|---|---|---|---|---|---|---|
| Heptacosanes | $C_{27}$ | | 2.053 | 2.770 | 373.00 | 0.8960 | 1.569 | 2.699 |
| Octacosanes | $C_{28}$ | | 1.925 | 2.695 | 387.00 | 0.8990 | 1.472 | 2.626 |
| Nonacosanes | $C_{29}$ | | 1.775 | 2.569 | 400.00 | 0.9020 | 1.357 | 2.503 |
| Tricontanes | $C_{30}$ | | 1.649 | 2.476 | 415.00 | 0.9050 | 1.260 | 2.412 |
| Hentriacontanes | $C_{31}$ | | 1.458 | 2.263 | 429.00 | 0.9090 | 1.114 | 2.205 |
| Dotriacontanes | $C_{32}$ | | 1.426 | 2.285 | 443.00 | 0.9120 | 1.090 | 2.226 |
| Tritriacontanes | $C_{33}$ | | 1.297 | 2.144 | 457.00 | 0.9150 | 0.992 | 2.089 |
| Tetratriacontanes | $C_{34}$ | | 1.294 | 2.204 | 471.00 | 0.9170 | 0.989 | 2.148 |
| Pentatriacontanes | $C_{35}$ | | 1.175 | 2.062 | 485.00 | 0.9200 | 0.898 | 2.009 |
| Hexatriacontanes plus | $C_{36+}$ | | 10.706 | 25.174 | 650.00 | 0.9913 | 8.183 | 24.528 |
| | | | 100.00 | 100.00 | | | 100.00 | 100.00 |
| Calculated MW | | 23.63 | | 276.43 | | | | 216.86 |

Compositional Grouping and Plus Fraction Properties

| Group | Mol % | wt % | MW | Density |
|---|---|---|---|---|
| C7+ | 71.56 | 95.88 | 290.57 | 0.8882 |
| C12+ | 53.92 | 86.07 | 324.97 | 0.8985 |
| C20+ | 32.64 | 65.30 | 433.88 | 0.9280 |
| C30+ | 14.53 | 37.62 | 561.56 | 0.9625 |
| C36+ | 8.18 | 24.53 | 650.00 | 0.9913 |

Zero Flash Results (5000 psig & 303 F.)

| | |
|---|---|
| Live oil density, g/cc | 0.8883 |
| GOR, scf/stb | 125.02 |
| Flashed oil density, g/cc | 0.8429 |
| Flashed oil MW | 287.60 |

TABLE 8

Oil Phase in Solution in FC-40 Composition (After mixing with FC-40 in the PVT cell)

| Component | | Flashed Gas Mole % | Flashed Oil Mole % | Flashed Oil Wt % | Molecular Weight | Specific Gravity | Live Oil* Mole % | Live Oil* Wt % |
|---|---|---|---|---|---|---|---|---|
| Nitrogen | $N_2$ | 0.986 | 0.000 | 0.000 | 28.01 | 0.8100 | 0.851 | 0.568 |
| Carbon Dioxide | $CO_2$ | 1.017 | 0.000 | 0.000 | 44.01 | 0.8270 | 0.877 | 0.920 |
| Hydrogen Sulphide | $H_2S$ | 0.000 | 0.000 | 0.000 | 34.08 | 0.7960 | 0.000 | 0.000 |
| Methane | $C_1$ | 69.727 | 0.015 | 0.002 | 16.05 | 0.3000 | 60.150 | 22.996 |
| Ethane | $C_2$ | 14.149 | 0.132 | 0.026 | 30.07 | 0.3560 | 12.223 | 8.756 |
| Propane | $C_3$ | 7.522 | 0.526 | 0.149 | 44.10 | 0.5010 | 6.561 | 6.893 |
| i-Butane | i-$C_4$ | 1.181 | 0.327 | 0.122 | 58.12 | 0.5570 | 1.064 | 1.473 |
| n-Butane | n-$C_4$ | 2.536 | 1.325 | 0.496 | 58.12 | 0.5790 | 2.372 | 3.284 |
| i-Pentane | i-$C_5$ | 0.943 | 1.391 | 0.646 | 72.15 | 0.6200 | 1.004 | 1.726 |
| n-Pentane | n-$C_5$ | 0.858 | 2.105 | 0.978 | 72.15 | 0.6260 | 1.029 | 1.769 |
| Hexanes | $C_6$ | 0.703 | 5.548 | 3.000 | 84.00 | 0.6900 | 1.369 | 2.739 |
| Heptanes | $C_7$ | 0.228 | 8.537 | 5.220 | 95.00 | 0.7270 | 1.370 | 3.100 |
| Octanes | $C_8$ | 0.104 | 16.177 | 11.142 | 107.00 | 0.7490 | 2.312 | 5.894 |
| Nonanes | $C_9$ | 0.031 | 11.577 | 9.017 | 121.00 | 0.7680 | 1.617 | 4.662 |
| Decanes | $C_{10}$ | 0.009 | 9.473 | 8.293 | 136.00 | 0.7820 | 1.309 | 4.242 |
| Undecanes | $C_{11}$ | 0.003 | 7.563 | 7.254 | 149.00 | 0.7930 | 1.042 | 3.697 |
| Dodecanes | $C_{12}$ | 0.000 | 5.865 | 6.154 | 163.00 | 0.8040 | 0.806 | 3.129 |
| Tridecanes | $C_{13}$ | | 5.296 | 6.000 | 176.00 | 0.8150 | 0.728 | 3.051 |
| Tetradecanes | $C_{14}$ | | 4.225 | 5.194 | 191.00 | 0.8260 | 0.580 | 2.641 |
| Pentadecanes | $C_{15}$ | | 3.555 | 4.736 | 207.00 | 0.8360 | 0.488 | 2.408 |
| Hexadecanes | $C_{16}$ | | 2.653 | 3.773 | 221.00 | 0.8430 | 0.364 | 1.919 |
| Heptadecanes | $C_{17}$ | | 2.208 | 3.368 | 237.00 | 0.8510 | 0.303 | 1.712 |
| Octadecanes | $C_{18}$ | | 1.936 | 3.103 | 249.00 | 0.8560 | 0.266 | 1.578 |
| Nonadecanes | $C_{19}$ | | 1.665 | 2.797 | 261.00 | 0.8610 | 0.229 | 1.422 |
| Eicosanes | $C_{20}$ | | 1.264 | 2.237 | 275.00 | 0.8660 | 0.174 | 1.137 |
| Heneicosanes | $C_{21}$ | | 1.058 | 1.968 | 289.00 | 0.8710 | 0.145 | 1.001 |
| Docosanes | $C_{22}$ | | 0.840 | 1.639 | 303.00 | 0.8760 | 0.115 | 0.833 |
| Tricosanes | $C_{23}$ | | 0.710 | 1.449 | 317.00 | 0.8810 | 0.098 | 0.737 |
| Tetracosanes | $C_{24}$ | | 0.589 | 1.255 | 331.00 | 0.8850 | 0.081 | 0.638 |
| Pentacosanes | $C_{25}$ | | 0.463 | 1.074 | 345.00 | 0.8880 | 0.066 | 0.546 |
| Hexacosanes | $C_{26}$ | | 0.414 | 0.957 | 359.00 | 0.8920 | 0.057 | 0.487 |
| Heptacosanes | $C_{27}$ | | 0.353 | 0.848 | 373.00 | 0.8960 | 0.049 | 0.431 |
| Octacosanes | $C_{28}$ | | 0.289 | 0.719 | 387.00 | 0.8990 | 0.040 | 0.366 |
| Nonacosanes | $C_{29}$ | | 0.250 | 0.644 | 400.00 | 0.9020 | 0.034 | 0.327 |
| Tricontanes | $C_{30}$ | | 0.212 | 0.566 | 415.00 | 0.9050 | 0.029 | 0.288 |
| Hentriacontanes | $C_{31}$ | | 0.159 | 0.440 | 429.00 | 0.9090 | 0.022 | 0.224 |
| Dotriacontanes | $C_{32}$ | | 0.153 | 0.437 | 443.00 | 0.9120 | 0.021 | 0.222 |

TABLE 8-continued

Oil Phase in Solution in FC-40 Composition (After mixing with FC-40 in the PVT cell)

| | | | | | | | |
|---|---|---|---|---|---|---|---|
| Tritriacontanes | $C_{33}$ | 0.129 | 0.379 | 457.00 | 0.9150 | 0.018 | 0.193 |
| Tetratriacontanes | $C_{34}$ | 0.120 | 0.365 | 471.00 | 0.9170 | 0.017 | 0.186 |
| Pentatriacontanes | $C_{35}$ | 0.106 | 0.332 | 485.00 | 0.9200 | 0.015 | 0.169 |
| Hexatriacontanes plus | $C_{36+}$ | 0.770 | 3.220 | 650.00 | 0.9913 | 0.106 | 1.637 |
| | | 100.00 | 100.00 | | | 100.000 | 100.000 |
| Calculated MW | | 23.92 | 155.35 | | | 41.978 | |

*Estimated based on mass balance calculation.

Compositional Grouping and Plus Fraction Properties

| Group | Mol % | wt % | MW | Density |
|---|---|---|---|---|
| C7+ | 12.50 | 48.88 | 164.13 | 0.8116 |
| C12+ | 4.85 | 27.28 | 205.31 | 0.8465 |
| C20+ | 1.09 | 9.42 | 364.35 | 0.9026 |
| C30+ | 0.23 | 2.92 | 540.45 | 0.9549 |
| C36+ | 0.11 | 1.64 | 650.00 | 0.9913 |

Zero Flash Results (5000 psig & 303 F.)

| | |
|---|---|
| GLR*, scf/stb | 152.40 |
| Flashed liquid density*, g/cc | 1.8500 |

*Liquid is mixture of live oil and FC-40
*FC-40 fluid density at STP

TABLE 9

Material Balance Calculation Basis for Table 8

INITIAL VOLUMETRIC CONDITIONS

| | | |
|---|---|---|
| Pressure: | 5015 psia | |
| Temperature: | 303.0 F. | |
| Reservoir fluid volume: | 60.00 cc | 0.4714 mole |
| Reservoir fluid density: | 0.5593 g/cc | |
| Displaced oil volume: | 20.30 cc | 0.0832 mole |
| Displaced oil density: | 0.8883 g/cc | |
| Oil phase in solution + FC-40: | 353.71 cc | 0.3882 mole |

OIL PHASE IN SOLUTION + FC-40 FLASH TEST VOLUMETRICS

| | | |
|---|---|---|
| Total flashed volume: | 20.84 cc | 5015 psia & 303 F. |
| Gas volume collected: | 467.51 cc | 14.696 psia & 60 F. |
| Totas Gas in solution (scaled) | 7933.78 cc | 0.3349 mole |
| Dead oil in solution by material balance | | 0.0533 mole |

TABLE 10

FC-40 Preparation

Composition

| Component | | Mole % | Wt % | Molecular Weight | Specific Gravity |
|---|---|---|---|---|---|
| Nitrogen | $N_2$ | 0.000 | 0.000 | 28.01 | 0.8100 |
| Carbon Dioxide | $CO_2$ | 0.000 | 0.000 | 44.01 | 0.8270 |
| Hydrogen Sulphide | $H_2S$ | 0.000 | 0.000 | 34.08 | 0.7960 |
| Methane | $C_1$ | 0.000 | 0.000 | 16.05 | 0.3000 |
| Ethane | $C_2$ | 0.042 | 0.017 | 30.07 | 0.3560 |
| Propene | $C_3$ | 0.033 | 0.019 | 44.10 | 0.5010 |
| i-Butane | $i-C_4$ | 0.000 | 0.000 | 58.12 | 0.5570 |
| n-Butane | $n-C_4$ | 0.000 | 0.000 | 58.12 | 0.5790 |
| i-Pentane | $i-C_5$ | 0.000 | 0.000 | 72.15 | 0.6200 |
| n-Pentane | $n-C_5$ | 0.000 | 0.000 | 72.15 | 0.6260 |
| Carbon Disulfide | $CS_2$ | 99.910 | 99.944 | 76.13 | n/a |
| Hexanes | $C_6$ | 0.000 | 0.000 | 84.00 | 0.6900 |
| Heptanes | $C_7$ | 0.000 | 0.000 | 95.00 | 0.7270 |
| Octanes | $C_8$ | 0.016 | 0.020 | 107.00 | 0.7490 |
| Nonanes | $C_9$ | 0.000 | 0.000 | 121.00 | 0.7680 |
| Decanes | $C_{10}$ | 0.000 | 0.000 | 136.00 | 0.7820 |
| Undecanes | $C_{11}$ | 0.000 | 0.000 | 149.00 | 0.7930 |
| Dodecanes | $C_{12}$ | 0.000 | 0.000 | 163.00 | 0.8040 |
| Tridecanes | $C_{13}$ | 0.000 | 0.000 | 176.00 | 0.8150 |
| Tetradecanes | $C_{14}$ | 0.000 | 0.000 | 191.00 | 0.8260 |
| Pentadecanes | $C_{15}$ | 0.000 | 0.000 | 207.00 | 0.8360 |
| Hexadecanes | $C_{16}$ | 0.000 | 0.000 | 221.00 | 0.8430 |
| Heptadecanes | $C_{17}$ | 0.000 | 0.000 | 237.00 | 0.8510 |
| Octadecanes | $C_{18}$ | 0.000 | 0.000 | 249.00 | 0.8560 |
| Nonadecanes | $C_{19}$ | 0.000 | 0.000 | 261.00 | 0.8610 |
| Eicosanes | $C_{20}$ | 0.000 | 0.000 | 275.00 | 0.8660 |
| Heneicosanes | $C_{21}$ | 0.000 | 0.000 | 289.00 | 0.8710 |
| Docosanes | $C_{22}$ | 0.000 | 0.000 | 303.00 | 0.8760 |
| Tricosanes | $C_{23}$ | 0.000 | 0.000 | 317.00 | 0.8810 |
| Tetracosanes | $C_{24}$ | 0.000 | 0.000 | 331.00 | 0.8850 |
| Pentacosanes | $C_{25}$ | 0.000 | 0.000 | 345.00 | 0.8880 |
| Hexacosanes | $C_{26}$ | 0.000 | 0.000 | 359.00 | 0.8920 |
| Heptacosanes | $C_{27}$ | 0.000 | 0.000 | 373.00 | 0.8960 |
| Octacosanes | $C_{28}$ | 0.000 | 0.000 | 387.00 | 0.8990 |
| Nonacosenes | $C_{29}$ | 0.000 | 0.000 | 400.00 | 0.9020 |
| Tricontanes | $C_{30}$ | 0.000 | 0.000 | 415.00 | 0.9050 |
| Hentriacontanes | $C_{31}$ | 0.000 | 0.000 | 429.00 | 0.9090 |
| Dotriacontanes | $C_{32}$ | 0.000 | 0.000 | 443.00 | 0.9120 |
| Tritriacontanes | $C_{33}$ | 0.000 | 0.000 | 457.00 | 0.9150 |
| Tetatriacontanes | $C_{34}$ | 0.000 | 0.000 | 471.00 | 0.9170 |
| Pentatriacontanes | $C_{35}$ | 0.000 | 0.000 | 485.00 | 0.9200 |
| Hexatriacontanes plus | $C_{36+}$ | 0.000 | 0.000 | 650.00 | 0.9913 |
| | | 100.00 | 100.00 | | |

| | | |
|---|---|---|
| Weight of Sample Used | 0.8401 | g |
| Internal Standard Added | 0.0095 | g |

The invention claimed is:

1. A method of assaying a test fluid for collecting reservoir core samples at reservoir temperature and pressure (RTP) and determining if said test fluid is inert at RTP, said method comprising:
  a) assaying a live oil to generate a first dataset using methods comprising at least one of:

i) determining a weight contribution of components of said live oil;
ii) determining a bubble point of said live oil;
iii) determining a density of a remaining oil when said live oil is flashed to standard temperature and pressure (STP) or ambient conditions;
iv) determining a weight contribution of gaseous components flashed from said live oil; or
v) determining total acid number (TAN), metal content, viscosity, asphaltene content, C7 content, nitrogen content, water content, carbon content, total contents, wax content, carbon residue content, conductivity, pour point, density at 15° C., salt content, sediment content, specific gravity, light end hydrocarbon content, mercaptan content, hydrogen content, total sulfur, hydrogen sulfide content or vapor pressure of said hydrocarbon phase or said remaining hydrocarbon phase;

b) assaying said live oil plus a test fluid mixed together and equilibrated at RTP to form hydrocarbon phase and a test fluid phase to generate a second dataset, using methods comprising at least one of:
i) determining a bubble point of said hydrocarbon phase;
ii) determining a weight contribution of components of said hydrocarbon phase;
iii) determining a density of a remaining hydrocarbon phase when said hydrocarbon phase is flashed to STP or ambient conditions;
iv) determining a weight contribution of gaseous components flashed from said hydrocarbon phase; or
v) determining total acid number (TAN), metal content, viscosity, asphaltene content, C7 content, nitrogen content, water content, carbon content, total contents, wax content, carbon residue content, conductivity, pour point, density at 15° C., salt content, sediment content, specific gravity, light end hydrocarbon content, mercaptan content, hydrogen content, total sulfur content, hydrogen sulfide content or vapor pressure of said hydrocarbon phase or said remaining hydrocarbon phase;

c) comparing said first dataset and said second dataset, wherein changes in said second dataset compared with said first dataset indicates that said test fluid is not inert, but no changes indicates said test fluid is inert and can be used to collect reservoir core samples at RTP.

2. The method of claim 1, wherein the weight contribution is determined with gas chromatography.

3. The method of claim 1, wherein the weight contribution of components of any fluid is determined with elemental composition and gas chromatography.

4. The method of claim 1, wherein the weight contribution of gaseous components is determined with gas chromatography.

5. The method of claim 1, wherein the weight contribution of components of any fluid is determined with elemental composition and gas chromatography with flame ionization detector (GC/FID).

6. The method of claim 1, wherein the density is determined using a High Pressure High Temperature (HPHT) densitometer at RTP.

7. The method of claim 1, wherein the bubble point is determined by stepping down the pressure from RTP and observing a pressure at which bubbles appear.

8. The method of claim 1, wherein the bubble point is determined by ASTM D2889-95 (2019).

9. The method of claim 1, wherein the RTP is an average temperature and pressure of a play in the reservoir.

10. The method of claim 1, wherein step a) and step b) assaying includes characterization of elements, C1-C40 components, the bubble point and the density.

11. The method of claim 10, wherein said characterization of elements and C1-C40 components are determined with elemental composition and gas chromatography.

12. The method of claim 10, wherein said characterization of elements and C1-C40 components are determined by elemental composition and gas chromatography with flame ionization detector (GC/FID).

13. The method of claim 10, wherein the density is determined using a High Pressure High Temperature (HPHT) densitometer at RTP.

14. The method of claim 10, wherein the bubble point is determined by stepping down a pressure from RTP and observing a pressure at which bubbles form.

15. The method of claim 10, wherein the bubble point is determined by ASTM D2889-95 (2019).

16. The method of claim 10, wherein the RTP is an average temperature and pressure of a play in the reservoir.

17. The method of claim 1, wherein step a) and step b) include assaying a composition, the density at 15° C., and the bubble point.

* * * * *

UNITED STATES PATENT AND TRADEMARK OFFICE
CERTIFICATE OF CORRECTION

Page 1 of 1

PATENT NO. : 12,385,888 B2
APPLICATION NO. : 17/888089
DATED : August 12, 2025
INVENTOR(S) : Martin C. Krueger et al.

It is certified that error appears in the above-identified patent and that said Letters Patent is hereby corrected as shown below:

In the Claims

On Column 21, Line 20, of Claim 1 "and equilibrated at RTP to form hydrocarbon phase and" should read as --- and equilibrated at RTP to form a hydrocarbon phase and ---

Signed and Sealed this
Ninth Day of December, 2025

John A. Squires
*Director of the United States Patent and Trademark Office*